US007803912B2

(12) United States Patent
Olson et al.

(10) Patent No.: US 7,803,912 B2
(45) Date of Patent: Sep. 28, 2010

(54) INCREASING THE STABILITY OF RECOMBINANT ADULT HUMAN APOHEMOGLOBIN

(75) Inventors: John S. Olson, Houston, TX (US); George N. Phillips, Jr., Madison, WI (US)

(73) Assignees: William Marsh Rice University, Houston, TX (US); Wisconsin Alumni Research Foundation, Madison, WI (US)

( * ) Notice: Subject to any disclaimer, the term of this patent is extended or adjusted under 35 U.S.C. 154(b) by 44 days.

(21) Appl. No.: 11/724,007

(22) Filed: Mar. 14, 2007

(65) Prior Publication Data

US 2007/0172924 A1    Jul. 26, 2007

Related U.S. Application Data

(63) Continuation of application No. PCT/US2005/032627, filed on Sep. 15, 2005.

(60) Provisional application No. 60/610,108, filed on Sep. 15, 2004, provisional application No. 60/610,110, filed on Sep. 15, 2004.

(51) Int. Cl.
*A61K 35/14* (2006.01)
(52) U.S. Cl. .................................. 530/385
(58) Field of Classification Search .............. 530/385
See application file for complete search history.

(56) References Cited

U.S. PATENT DOCUMENTS

| | | | |
|---|---|---|---|
| 5,028,588 A * | 7/1991 | Hoffman et al. ............... | 514/6 |
| 5,239,061 A | 8/1993 | Fronticelli et al. ............ | 530/385 |
| 5,240,831 A | 8/1993 | Barnes ....................... | 435/69.1 |
| 5,286,638 A | 2/1994 | Tanaka et al. ................ | 435/192 |
| 5,827,693 A | 10/1998 | De Angelo et al. ........... | 435/69.6 |
| 6,022,849 A | 2/2000 | Olson et al. .................. | 514/6 |
| 6,114,505 A | 9/2000 | Olson et al. .................. | 530/385 |
| 6,172,039 B1 | 1/2001 | De Angelo et al. ........... | 514/6 |
| 6,204,035 B1 | 3/2001 | Olson et al. .................. | 435/69.1 |
| 6,455,676 B1 | 9/2002 | Weickert et al. ............. | 530/385 |
| 7,019,406 B2 | 3/2006 | Huang et al. ................. | 257/778 |
| 7,049,406 B2 | 5/2006 | Weickert et al. ............. | 530/385 |
| 2005/0048479 A1 | 3/2005 | Gandhi et al. ................ | 435/6 |
| 2007/0154993 A1 | 7/2007 | Olson et al. .................. | 435/69.6 |
| 2007/0166792 A1 | 7/2007 | Olson et al. .................. | 435/69.1 |

FOREIGN PATENT DOCUMENTS

WO         96/41885         12/1996

OTHER PUBLICATIONS

Fronticelli et al. 1995; Allosteric modulation by tertiary structure in mammalian hemoglobins. J. Biol. Chem. 270(51): 30588-30592.*
Dumoulin et al. 1998; The N-terminal sequence affects distant helix interaction in hemoglobin. J. Biol. Chem. 273(52): 35032-35038.*
Abbasi et al. 1986; The primary structure of sperm whale hemoglobin (Physeter catodon, Cetacea). Bio. Chem Hoppe-Seyler 367: 355-361.*
Ackers "Deciphering The Molecular Code Of Hemoglobin Allostery" Dept. of Biochemistry and Biophysics, Washington University (pp. 185-253), 1998.
Ackers "Energetics Of Subunit Assembly And Ligand Binding In Human Hemoglobin" Dept. of Biology and McCollum Pratt Institute, The Johns Hopkins University (pp. 331-346), 1980.
Adachi et al. "Consequence of β16 and β112 Replacements on the Kinetics of Hemoglobin Assembly" Biochemical and Biophysical Research Communications, vol. 289 (pp. 75-79), 2001.
Adachi et al. "Significance of β16 His (G18) at α1β1 Contact Sites for αβ Assembly and Autoxidation of Hemoglobin" Biochemistry, vol. 42 (pp. 10252-10259), Apr. 16, 2003.
Antonini, E. and Brunori M., "Hemoglobin and Myoglobin in Their Reactions with Ligands", North-Holland Publishing Company, Amsterdam, London, 1971, (pp. 110-119, 126-129), 1971.
Ascoli et al. "Preparation and Properties of Apohemoglobin and Reconstituted Hemoglobins" Methods in Enzymology, vol. 76 (pp. 72-87), 1981.
Barrick et al. "Three-State Analysis of Sperm Whale Apomyoglobin Folding" Biochemistry, vol. 32 (pp. 3790-3796), Feb. 1, 1993.
Benesch et al. "The Stability of the Heme-Globin Linkage in Some Normal, Mutant, and Chemically Modified Hemoglobins" The Journal of Biological Chemistry, vol. 265, No. 25 (pp. 14881-14885), Feb. 9, 1990.
Bunn et al. "Exchange of Heme among Hemoglobins and between Hemoglobin and Albumin" The Journal of Biological Chemistry, vol. 243, No. 3 (pp. 465-475), Jun. 19, 1967.
Bunn et al. "Electrostatic interactions in the assembly of haemoglobin" Nature 306 (pp. 498-500), Dec. 1983.
M. Bunn, H.F. and Forget B.G., "Hemoglobin: Molecular, Genetic and Clinical Aspects", W.B. Saunders Company, Philadelphia, 1986, (pp. 68-75).
Chu et al. "Interaction of Human Apohemoglobin with Inositol Hexaphosphate" The Journal of Biological Chemistry, vol. 254, No. 2 (pp. 371-376), Jan. 25, 1979.
Dodson et al. "Apomyoglobin as a molecular recognition surface: expression, reconstitution and crystallization of recombinant porcine myoglobin in *Excherichia coli*" Protein Engineering vol. 2, No. 3 (pp. 233-237), 1988.
Edelstein "Cooperative Interactions of Hemoglobin" Annu Review Biochem 44 (pp. 209-232), 1975.
Eliezer et al. "Native and Non-native Secondary Structure and Dynamics in the pH 4 Intermediate of Apomyoglobin" Biochemistry 39 (pp. 2894-2901), Jan. 7, 2000.

(Continued)

*Primary Examiner*—Karen Cochrane Carlson
(74) *Attorney, Agent, or Firm*—Baker Botts L.L.P.

(57) ABSTRACT

The disclosure relates to recombinant adult human apohemoglobin (apo-rHb) in which the stability has been increased by replacement of an amino acid with a counterpart from another organism, such as a deep sea diving mammal. This mutated apo-rHb may be more stable and/or give higher production yields than unmutated adult human apo-rHb. The mutated apo-rHb may be produced in microorganisms, such as *E. coli* or yeast cells, or animal erythroid cells. Some apo-rHb of the present disclosure may be used as part of a blood substitute.

11 Claims, 6 Drawing Sheets

OTHER PUBLICATIONS

Eliezer et al. "Populating the equilibrium molten globule state of apomyoglobin under conditions suitable for structural characterization by NMR" Federation of European Biochemical Sciences Letter 417 (pp. 92-96), Sep. 11, 1997.

Eliezer et al. "Structural and dynamic characterization of partially folded states of apomyoglobin and implications for protein folding" Nature Structural Biology 5 (pp. 148-155), Feb. 1998.

Garcia et al. "Changes in Apomyoglobin Folding Pathway Caused by Mutation of the Distal Histidine Residue" Biochemistry 39 (pp. 11227-11237), 2000.

Gattoni et al. "Stability of the Heme-Globin Linkage in αβ Dimers and Isolated Chains of Human Hemoglobin" The Journal of Biological Chemistry, vol. 271, No. 17 (pp. 10130-10136), Apr. 26, 1996.

Gibson et al. "Kinetic Studies on the Reaction between Native Globin and Haem Derivatives" Biochem J 77 (pp. 328-341), 1960.

Gibson et al. "Rates of Reaction of Native Human Globin with Some Hemes" The Journal of Biological Chemistry, vol. 258, No. 4 (pp. 1384-1388), Apr. 1963.

Hargrove et al. "Stability of Myoglobin: A Model for the Folding of Heme Proteins" Biochemistry 33 (pp. 11767-11775), Jun. 14, 1994.

Hargrove et al. "The Association Rate Constant for Heme Binding to Globin is Independent of Protein Structure" Biochemistry 35 (pp. 11293-11299), 1996.

Hargrove et al. "The Stability of Holomyoglobin is Determined by Heme Affinity" Biochemistry 35 (pp. 11310-11318), 1996.

Hargrove et al. "Quaternary Structure Regulates Hemin Dissociation from Human Hemoglobin" Journal of Biololgical Chemistry vol. 272, No. 28 (pp. 17385-17389), 1997.

Hughson et al. "Structural Characterization of a Partly Folded Apomyoglubin Intermediate" Science vol. 249 (pp. 1544-1548), 1990.

Ip et al. "Kinetics of Deoxyhemoglobin Subunit Dissociation Determined by Haptoglobin Binding: Estimation of the Equilibrium Constant from Forward and Reverse Rates" Biochemistry vol. 15, No. 3 (pp. 654-660), 1976.

Ip et al. "Thermodynamic Studies on Subunit Assembly in Human Hemoglobin" The Journal of Biological Chemistry vol. 252, No. 1 (pp. 82-87), 1977.

Jennings et al. "Esterification of the Propionate Groups Promotes α / β Hemoglobin Chain Homogeneity of CN-hemin Binding" Biochemical and Biophysical Research Communications 293 (pp. 1354-1357), 2002.

Joshi, J "Role of α and β Carboxyl-terminal Residues in the Kinetics of Human Oxyhemoglobin Dimer Assembly" The Journal of Biological Chemisstry, vol. 269, No. 11 (pp. 8549-8553), 1994.

Kooyman et al. "The Physiological Basis of Diving to Depth: birds and Mammals" Annu. Rev. Physiol., vol. 60 (pp. 19-32), 1998.

Kowalczyck et al. "Dimensions in Solution of Pryidoxylated Apohemoglobin" Biochemistry 22 (pp. 4805-4809), 1983.

Lloyd et al. "Formation of Sulphmyoglobin During Expression of Horse Heart Myoglobin in *Escherichia coli*" Federation of European Biochemical Societies Letters 340 (pp. 281-286), 1994.

Looker et al. "Expression of Recombinant Human Hemoglobin in *Escherichia coli*" Methods in Enzymology, vol. 231 (pp. 364-374), 1994.

McDonald et al. "Structural, Functional, and Subunit Assembly Properties of Hemoglobin Attleboro [α138 (H21) Ser→Pro], a Variant Possessing a Site Mutation at a Critical C-Terminal Residue" Biochemistry 29 (pp. 173-178), 1990.

McDonald et al. "The Kinetics of Assembly of Normal and Variant Human Oxyhemoglobins" The Journal of Biological Chemistry, vol. 262, No. 13 (pp. 5951-5956), 1987.

McDonald et al. "Subunit Assembly of Normal and Variant Human Hemoglobins" the Red Cell: Sixth Ann Arbor Conference 1984 (pp. 2-11), 1984.

McGovern et al. "Aggregation of Deoxyhemoglobin Subunits" The Journal of Biological Chemistry, vol. 251 (pp. 7871-7879), 1976.

Moulton et al. "Kinetics of Human Apohemoglobin Dimer Dissociation" Biochemical and Biophysical Research Communications, vol. 199, No. 3 (pp. 1278-1283), 1994.

Mrabet et al. "Dissociation of Dimers of Human Hemoglobins A and F into Monomers" The Journal of Biological Chemictry, vol. 261, No. 3 (pp. 1111-1115), 1984.

Mrabet et al. "Electrostatic Attraction Governs the Dimer Assembly of Human Hemoglobin" The Journal of Biological Chemistry, vol. 261, No. 11 (pp. 5222-5228), 1986.

Musto et al. "Voiding of Aplysia limacina Apomyoglobin Involves an Intermediate in Common with Other Evoluionarily Distant Globins" Biochemistry 43 (pp. 230-236), 2004.

Nishimura et al. "Role of the B Helix in Early Folding Events in Apomyoglobin: Evidence from Site-directed Mutagenesis for Native-like Long Range Interactions" J Mol Biol 334 (pp. 293-307), 2003.

Nishimura et al. "Conservation of Folding Pathways in Evolutionarily Distant Globin Sequences" Nature Structure Biology, vol. 7, No. 8 (pp. 679-686), 2000.

Olson et al. "Protein Engineering Strategies For Designing More Stable Hemoglobin-Based Blood Substitutes" Artificial Cells, Blood Substitutes, and Immobilization Biotechnology 25 (pp. 227-241), 1997.

O'Malley et al. "Monitoring the Effect of Subunit Assembly on the Structural Flexibility of Human Alpha Apohemoglobin by Steady-State Fluorescence" The Journal of Protein Chemistry, vol. 13, No. 6 (pp. 561-567), 1994.

Oton et al. "Fluorescence Studies of Internal Rotation in Apohemoglobin α-Chains" Archives of Biochemistry Biophysics, vol. 228, No. 2 (pp. 519-524), Feb. 1, 1984.

Perutz. "Mechanisms Regulating the Reactions of Human Hemoglobin with Oxygen and Carbon Monoxide" Annual Review of Physiology 52 (pp. 1-25), 1990.

Perutz "Stereochemistry of Cooperative Effects in Haemoglobin" Nature, vol. 228 (pp. 726-739), Nov. 21, 1970.

Ramsay et al. "Modified Spectrophotometer for Multi-Dimensional Circular Dichroism/Fluoresence Data Acquisition in Titration Experiments: Application to the pH and Guanidine-HCl Induced Unfolding of Apomyoglobin" Biophysical Journal, vol. 69 (pp. 701-707), Aug. 1998.

Rose et al. "The Kinetic Mechanism of Heme Binding to Human Apohemoglobin" The Journal of Biological Chemistry, vol. 258, No. 7 (pp. 4298-4303), Apr. 10, 1983.

Sassaroli et al. "Specialized Functional Domains in Hemoglobin: Dimensions in Solution of the Apohemoglobin Dimer Labeled with Fluorescein Iodoacetamide" Biochemistry 23 (pp. 2487-2491), 1984.

Shaeffer et al. "Dimer-Monomer Dissociation of Human Hemoglobin A" The Journal of Biological Chemistry, vol. 259, No. 23 (pp. 14544-14547), Dec. 10, 1984.

Scott et al. "The Stabilities of Mammalian Apomyoglobins Vary over a 600-Fold Range and Can Be Enhanced by Comparative Mutagenesis" The Journal of Biological Chemistry, vol. 275, No. 35 (pp. 27129-27136), Sep. 1, 2000.

Smith, "The Effects on Amino Acid Substitution on Apomyoglobin Stability, Folding Intermediates, and Holoprotein Expression", Ph.D. Dissertation, Biochemistry & Cell Biology, Rice University Houston Texas, 2003.

Snyder "Respiratory Adaptions in Diving Mammals" Respiration Physiology 54 (pp. 296-294), 1983.

Springer et al. "High-level expression of sperm whale myoglobin in *Escherichia coli*" Proc. Natl. Acad. Sci., vol. 84 (pp. 8961-8965), Dec. 1987.

Tang et al. "Disruption of the Heme Iron-Proximal Histidine Bond Requires Unfolding of Deoxymyoglobin" Biochemistry 37 (pp. 7047-7056), Feb. 26, 1998.

Varadarajan et al. "Cloning, expression in *Excherichia coli*, and reconstitution of human myoglobin" Proc. Natl. Acad. Sci., vol. 82 (pp. 5681-5684), Sep. 1985.

Vasudevan et al. "Ordered Heme Binding Ensures the Assembly of Fully Functional Hemoglobin: A Hypothesis" Current Protein and Peptide Science 3 (pp. 461-466), 2002.

Vasudevan et al. "Spectral Demonstration of Semihemoglobin Formation during CN-Hemin Incorporation into Human Apohemoglobins" The Journal of Biological Chemistry, vol. 272, No. 1 (pp. 517-524), Jan. 3, 1997.

Vasudevan et al. "Wavelength-Dependent Spectral Changes Accompany CN-hemin Binding to Human Apohemoglobin" Journal of Protein Chemistry, vol, 19, No. 7 (pp. 583-590), 2000.

Waks et al. "Influence of Prosthetic Groups on Protein Folding and Subunit Assembly" The Journal of Biological Chemistry, vol. 248, No. 18 (pp. 6462-6470), Sep. 25, 1973.

Wiedermann et al. "Acceleration of Tetramer Formation by the Binding of Inositol Hexaphosphate to Hemoglobin Dimers" the Journal of Biological Chemistry, vol. 250, No. 13 (pp. 5273-5275), Jul. 10, 1975.

Yamaguchi et al. "Surface and Interface β-Chain Residues Synergistically Affect Hemoglobin Assembly" Biochemical and Biophysical Research Communications 270 (pp. 683-687), Mar. 7, 2000.

Zapol et al. "Regional blood flow during simulated diving in the conscious Weddell seal" J Applied Physiol, the American Physiological Society 47 (pp. 968-973), 1979.

PCT International Preliminary Report on Patentability, PCT/US2005/032627, 5 pgs, Mailing Date Mar. 29, 2007.

Adachi et al. "Assembly of γ- with α-Globin Chains to Form Human Fetal Hemoglobin in Vitro and in Vivo" J Biol Chem, vol. 275, Issue 17 (16 pages), Apr. 28, 2000.

Andrews et al. "Bacterial iron homeostasis" FEMS Microbiology Review 27 (pp. 215-237), 2003.

Bagg et al. "Ferric Uptake Regulation Protein Acts as a Repressor, Employing Iron (II) as a Cofactor To Bind the Operator of an Iron Transport Operon in *Escherichia coli*" Biochemistry, vol. 26 (pp. 5471-5477), 1987.

Baudin-Creuza et al. "Transfer of Human α- to β-Hemoglobin via Its Chaperone Protein" The Journal of Biological Chemistry, vol. 279, No. 35 (pp. 36530-36533), Aug. 27, 2004.

Daskaleros et al. "Iron Uptake in *Plesiomonas shigelloides*: Cloning of the Genes for the Heme-Iron Uptake System" Infection and Immunity, vol. 59, No. 8 (pp. 2706-2711), Aug. 1991.

dos Santos et al. "Expression of α-hemoglobin stabilizing protein gene during human erythropoiesis" Experimental Hematology, vol. 32 (pp. 157-162), 2004.

Dou et al. "Myoglobin as a model system for designing heme protein based blood substitutes" Biophysical Chemistry 98 (pp. 127-148), 2002.

Feng et al. Molecular Mechanism Of AHSP-Mediated Stabilization of α-Hemoglobin, Cell, vol. 119 (pp. 629-640), Nov. 24, 2004.

Feng et al. "Structure of Oxidized α-Haemoglobin Bound to AHSP Reveals a Protective Mechanism for Haem" Nature Publishing Group, vol. 435 (pp. 697-701), Jun. 2, 2005.

Gell et al. "Biophysical Characterization of the α-Globin Binding Protein α-Hemoglobin Stabilizing Protein" The Journal of Biological Chemistry, vol. 277, No. 43 (pp. 40602-40609), Oct. 25, 2002.

Genco et al. "Emerging strategies in microbial haem capture" Molecular Microbiology, vol. 39 (pp. 1-11), 2001.

Ghigo et al. "A New Type of Hemophore-Dependent Heme Acquisition System of *Serratia marcescens* Reconstituted in *Escherichia coli*" Journal of Bacteriology, vol. 179, No. 11 (pp. 3572- 3579), Jun. 1997.

Griggs et al. "Mechanism for Iron-Related Transcription of the *Escherichia coli cir* Gene: Metal-Dependent Binding of Fur Protein to the Promoters" Journal of Bacteriology, vol. 171, No. 2 (pp. 1048-1054), Feb. 1989.

Henderson et al. "Characterization of the *Plesiomonas shigelloides* Genes Encoding the Heme Iron Utilization System" Journal of Bacteriology, vol. 183, No. 9 (pp. 2715-2723), May 2001.

Henderson et al. "Characterization of the *Vibrio cholerae* Outer Membrane Heme Transport Protein HutA: Sequence of the Gene, Regulation of Expression, and Homology to the Family of TonB-Dependent Proteins" Journal of Bacteriology, vol. 176, No. 11 (pp. 3269-3277), Jun. 1994.

Henderson et al. "Cloning and characterization of the *Vibrio cholerae* genes encoding the utilization of iron from haemin and haemoglobin" Molecular Microbiology, vol. 7 (pp. 461-469), 1993.

Henderson et al. "*Vibrio cholerae* Iron Transport Systems: Roles of Heme and Siderophore Iron Transport in Virulence and Identification of a Gene Associated with Multiple Iron Transport Systems" Infection and Immunity, vol. 62, No. 11 (pp. 5120-5125), Nov. 1994.

International Preliminary Report on Patentability and Written Opinion for International Application No. PCT/US2005/032627 (5 pages), Mar. 29, 2007.

International Preliminary Report on Patentability and Written Opinion for International Application No. PCT/US2005/033027 (6 pages), Mar. 29, 2007.

International Preliminary Report on Patentability and Written Opinion for International Application No. PCT/US2005/033028 (6 pages), Mar. 29, 2007.

International Search Report and Written Opinion for International Application No. PCT/US2005/032627 (8 pages), Mar. 14, 2006.

International Search Report and Written Opinion for International Application No. PCT/US2005/033027 (9 pages), Nov. 1, 2006.

International Search Report and Written Opinion for International Application No. PCT/US2005/033028 (11 pages), Oct. 3, 2006.

Ip et al., "Kinetics of Deoxyhemoglobin Subunit Dissociation Determined by Haptoglobin Binding: Estimation of the Equilibrium Constant from Forward and Reverse Rates" Biochemistry, vol. 15, No. 3 (pp. 654-660), 1976.

Kihm et al., "An Abundant Erythroid Protien that Stabilizes Free Alpha-Hemoglobin" Nature, vol. 417, (pp. 758-763), Jun. 13, 2002.

Kong et al., "Loss of α-hemoglobin-stabilizing protein impairs erythropoiesis and exacerbates β-thalassemia" The Journal of Clinical Investigation, vol. 114, No. 10 (pp. 1457-1466), Nov. 2004.

Létoffé et al. "Free and Hemophore-Bound Heme Acquisitions through the Outer Membrane Receptor HasR Have Different Requirements for the TonB-ExbB-ExBD Complex" Journal of Bacteriology, vol. 186, No. 13 (pp. 4067-4074), Jul. 2004.

Light et al. "The Effects of Lipid Composition on the Rate and Extent of Heme Binding to Membranes" The Journal of Biological Chemistry, vol. 265, No. 26 (pp. 15632-15637), 1990.

Light et al. "Transmembrane Movement of Heme" The Journal of Biological Chemistry, vol. 265, No. 26 (pp. 15623-15631), 1990.

Litwin et al. "Role of Iron in Regulation of Virulence Genes" Clinical Microbiology Reviews, vol. 6, No. 2 (pp. 137-149), Apr. 1993.

Luzzatto et al. "Haemoglobin's Chaperone" Nature, vol. 417 (pp. 703-705), Jun. 13, 2002.

McGovern et al. "Aggregation of Deoxyhemoglobin Subunits*" The Journal of Biological Chemistry, vol. 251, No. 24 (pp. 7871-7879), Jul. 1976.

Mills et al. "Genetics and Regulation of Heme Iron Transport in *Shigella dysenteriae* and Detection of an Analogous System in *Escherichia coli* O157:H7" Journal of Bacteriology, vol. 177, No. 11 (pp. 3004-3009), Jun. 1995.

Mourino et al. "Characterization of Heme Uptake Cluster Genes in the Fish Pathogen *Vibrio anguillarum*" J Bacteriol. vol. 186, No. 18 (1 page), Sep. 2004.

Olson et al. "No Scavenging and the Hypertensive Effect of Hemoglobin-based Blood Substitutes" Free Radical Biology & Medicine, vol. 36, No. 6 (pp. 685-697), 2004.

O'Malley et al. "Fluorescence Studies of Normal and Sickle Beta Apohemoglobin Self-Association" Journal of Protein Chemistry, vol. 13, No. 7 (pp. 585-590), May 11, 1994.

Paquelin et al. "Characterization of HasB, a *Serratia marcescens* TonB-like protein specifically involved in the haemophore -dependent haem acquisition system" Molecular Microbiology, vol. 42, No. 4 (pp. 995-1005), 2001.

Pohl et al. "Architecture of a protein central to iron homeostasis: crystal structure and spectroscopic analysis of the ferric uptake regulator" Molecular Microbiology, vol. 47 (pp. 903-915), 2003.

Postle et al. "Touch and go: tying TonB to transport" Molecular Microbiology, vol. 49 (pp. 869-882), 2003.

Reeves et al. "TonB Is Required for Intracellular Growth and Virulence of *Shigella dysenteriae*" Infection and Immunity, vol. 68, No. 11 (pp. 6329-6336), Nov. 2000.

Santiveri et al. "NMR Structure of the α-Hemoglobin Stabilizing Protein" The Journal of Biological Chemistry, vol. 279, No. 33 (pp. 34963-34970), Aug. 13, 2004.

Seliger et al. "The two TonB systems of *Vibrio cholerae*: redundant and specific functions" Molecular Microbiology, vol. 39 (pp. 801-812), 2001.

Shen et al. "Production of human normal adult and fetal hemoglobins in *Escherichia coli*" Protein Engineering, vol. 10 (1 page), 1997.

Stojiljkovic et al. "Hemin uptake system of *Yersinia enterocolitica*: similarities with other TonB-dependent systems in Gram-negative bacteria" The EMBO Journal, vol. 11, No. 12 (pp. 4359-4367), 1992.

Stojiljkovic et al. "Processing of Heme and Heme-Containing Proteins by Bacteria" DNA and Cell Biology, vol. 21, No. 4 (pp. 281-295), 2002.

Thompson et al. "Molecular Characterization of the Hemin Uptake Locus (*hmu*) from *Yersinia pestis* and Analysis of *hmu* Mutants for Hemin and Hemoprotein Utilization" Infection and Immunity, vol. 67, No. 8 (pp. 3879-3892), Aug. 1999.

Thunell et al. "Porphyrins, porphyrin metabolism, and porphyrias. I. Update" Scand J Clin Lab Invest, vol. 60, Issue 7, (pp. 509-540), Nov. 2000.

Torres et al. "Haem iron-transport system in enterohaemorrhagic *Escherichia coli* O157:H7" Molecular Microbiology, vol. 23 (pp. 825-833), 1997.

Varnado et al. "System for the expression of recombinant hemoproteins in *Escherichia coli*" Protein Expression and Purification 35 (pp. 76-83), 2004.

Villaloboz et al. "0-083. Using *Escherichia coli* Containing the *Plesiomonas shigelloides* Heme Transport System to Increase the Production of Myoglobin" Abstracts of the General Meeting of the American Society for Microbiology, vol. 103, Abstr 0-083; Issn: 1060-2011 (p. 482), May 20, 2003.

Volkmar et al. "Iron transport and signaling in *Escherichia coli*" FEBS Letters 529 (pp. 78-85), 2002.

Wycuff et al. "Generation of an AraC-*ara*BAD Promoter-Regulated T7 Expression System[1]" Analytical Biochemistry 277 (pp. 67-73), Jun. 7, 1999.

* cited by examiner

US 7,803,912 B2

INCREASING THE STABILITY OF RECOMBINANT ADULT HUMAN APOHEMOGLOBIN

RELATED APPLICATION

This application is a continuation of International Application No. PCT/US2005/032627, filed on Sep. 15, 2005, which claims priority to U.S. Provisional Patent Application No. 60/610,108, filed on Sept. 15, 2004 and U.S. Provisional Patent Application No. 60/610,110, filed on Sep. 15, 2004, the full disclosures of which are incorporated herein by reference.

STATEMENT OF GOVERNMENT INTEREST

The present invention was made with United States government support awarded by the following agencies: NIH AR040252, NIH R01 HL047020 and NIH GM35649. The U.S. Government has certain rights in this invention.

TECHNICAL FIELD

The present disclosure relates to compositions and/or methods of producing compositions that include a form of hemoglobin.

BACKGROUND

Hemoglobin (Hb) is responsible for carrying and delivering oxygen to tissues and organs in animals and has been used in development of an effective and safe oxygen carrier as an alternative to blood transfusion. Hb can be obtained easily in large quantities from bovine sources, or can be produced transgenically, so the raw material is not limiting. Such forms of Hb, however, may have numerous serious side effects when transfused into a human patient. For example, raw Hb may cause vasoconstriction, abdominal pain, and acute kidney failure. In addition, products may cause elevation of blood pressure and other problems associated with interference with smooth muscle regulation.

Some of these effects may stem from the toxicity of Hb when it is outside of a red blood cell (erythrocyte). In addition, Hb outside of a red blood cell is rapidly broken down from its tetrameric form into dimers and monomers. These products may be taken up by the kidney and impair nephrological functions.

SUMMARY

Therefore, a need exists for oxygen delivery compositions that are safer, more clinically effective, and/or more economically produced.

The present disclosure, according to some example embodiments, relates to hemoglobin (rHb) and/or apohemoglobin (apo-rHb) in which at least a portion of the amino acid sequence (e.g., one or more amino acids) has been modified to match a counterpart from another amino acid sequence (e.g., another metal-binding protein). If more than one counterpart amino acid is used, the amino acids may be contiguous or discontiguous. According to some embodiments, a counterpart may include any metal-binding protein from any species. For example, counterparts may include human or non-human iron-binding proteins. Amino acids and/or amino acid sequences may be modified by any available means. For example, an amino acid and/or amino acid sequence may be modified by post-synthesis chemical modification. An amino acid and/or amino acid sequence may be may also be modified by modifying an encoding nucleic acid. An amino acid and/or amino acid sequence may be may also be modified by appropriate substitution during ribosomal or non-ribosomal synthesis.

The present disclosure, according to one example embodiment, relates to recombinant adult human apohemoglobin (apo-rHb) in which the stability has been increased by replacement of at least one amino acid with a counterpart from sperm whale α hemoglobin or β hemoglobin or human fetal γ hemoglobin. This mutated apo-rHB may be more stable and/or give higher production yields than unmutated adult human apo-rHb. Some apo-rHb of the present disclosure may be used as part of a blood substitute.

In other example embodiments, more stable human α and β globins are constructed by mutations of adult human rHb that are based on the naturally occurring amino acids found in adult hemoglobins of sperm whales (SW Hb) (and other deep diving mammals) and replacements found in human fetal hemoglobin (HbF). Resistance to unfolding, degradation, and precipitation may increase production yields in *E. coli* and other microorganisms, including other bacteria and yeasts, and in animal erythroid cells, such as mammalian erythroid cells. In some embodiments, the production of intact, usable rHb may be increased from the current level of 5-10% of *E. coli* total soluble protein to 30% or more.

Thus, some example embodiments of the present disclosure relate to rHb production cells, tissues, or animals in which apo-rHb contains at least one amino acid mutation in the adult human α or β hemoglobin subunit introduced from a sperm whale or deep diving mammal hemoglobin or human fetal hemoglobin, such that the mutated apo-rHb is more resistant to denaturation and thus more stable than unmutated adult human rHb.

In some embodiments, the disclosure provides a method of producing a stabilized apohemoglobin subunit comprising modifying at least a portion of the amino acid sequence of adult human apohemoglobin to match a counterpart from an apohemoglobin from another organism, wherein a stabilized apohemoglobin is produced. For example, the modifying may comprise forming a nucleic acid encoding substantially an adult human apohemoglobin subunit with at least one variant amino acid that matches its counterpart amino acid of an apohemoglobin from another organism and expressing said nucleic acid in *E. coli*, another microorganism, or animal erythroid cells. In this context, a variant amino acid may be one that differs from the wild-type amino acid and matches (e.g., is identical to) the amino acid at the corresponding position in a subunit from another organism.

Some example embodiments may relate to nucleic acids that encode modified apo-rHb. These embodiments may also encode at least two different hemoglobin subunits for co-expression in the same cell to produce apo-rHb. Still other example embodiments relate to systems including cells, such as *E. coli* cells, other microorganisms, or animal erythroid cells, for production of a more degradation-resistant mutated apo-rHb. These systems may also exhibit increased rHb production and fewer degradation products when compared with similar systems for production of unmutated adult human apo-rHb. Other embodiments relate to methods of making the above cells and nucleic acids as well as to methods of producing mutated apo-rhb.

In specific example embodiments, at least one of the following amino acid mutations may be made (the amino acids are specified by their helical location, i.e., A13 represents the thirteenth position along the A helix as indicated in FIG. 3):

α GlyA13 to Ala(Ser)
α GlyB3 to Ala (Asp, Glu, Asn)
α CE corner mutations
α CysG11 to Ser, Thr, Val β GlyA13 to Ala(Ser)
β ProD2 to Ala
β GlyD7 to Lys
β GlyE13 to Ala(Thr, Asp)
β CysG14 to Val, Thr, Ser, Ile
β ProH3 to Glu, Ala (Gln)
β CysG14 to Thr
β HisG18 to Ile(Leu, Ala)
β ProH3 to Glu
β TyrH8 to Trp(Leu)
β ValH11 to Met(Leu, Phe),
and any combination thereof.

According to some embodiments of the disclosure, at least one amino acid is modified to match the hemoglobin of another species. In some embodiments, two or more amino acids are modified to match the hemoglobin of another species. In some embodiments, three or more amino acids are modified to match the hemoglobin of another species. In some embodiments, no more than five amino acids are modified to match the hemoglobin of another species. In some embodiments, no more than ten amino acids are modified to match the hemoglobin of another species. In some embodiments, no more than fifteen amino acids are modified to match the hemoglobin of another species. In some embodiments, no more than twenty amino acids are modified to match the hemoglobin of another species.

BRIEF DESCRIPTION OF THE DRAWINGS

The present disclosure may be better understood through reference to the following detailed description, taken in conjunction with the following figures in which:

FIG. 3A illustrates the expression of wild-type myoglobin (Mb). The top graph shows the raw absorbance data for a typical assay of *E. coli* cells expressing wild-type sperm whale myoglobin. The bottom graph shows the free CO-heme has a broad Soret absorbance band at 412 nm, readily oxidizes to 4-coordinate hemin with a very broad peak at ~380 nm, and does not interfere with the HbCO derivative spectrum.

FIG. 3B illustrates the correlation between the $-\log(K_{NU})$, which is a direct, in vitro measure of the stability of the apoprotein, measured in 200 mP KPi and the log(relative expression level) for 35 single, double, and triple mutants of sperm whale myoglobin.

FIG. 5A illustrates that almost twice as much of the β(G16A) mutant is expressed compared to wild-type rHb0.0. This two-fold enhancement of expression occurs in the absence and presence of heme.

FIG. 5B illustrates co-expression of the hug genes (+Dip) enhances the production of both proteins significantly, but again the more stable β (Gly16(A13)Ala) mutant still expresses to a much higher level demonstrating that enhance of resistance to denaturation does result in higher expression levels.

DETAILED DESCRIPTION

Figure 1:
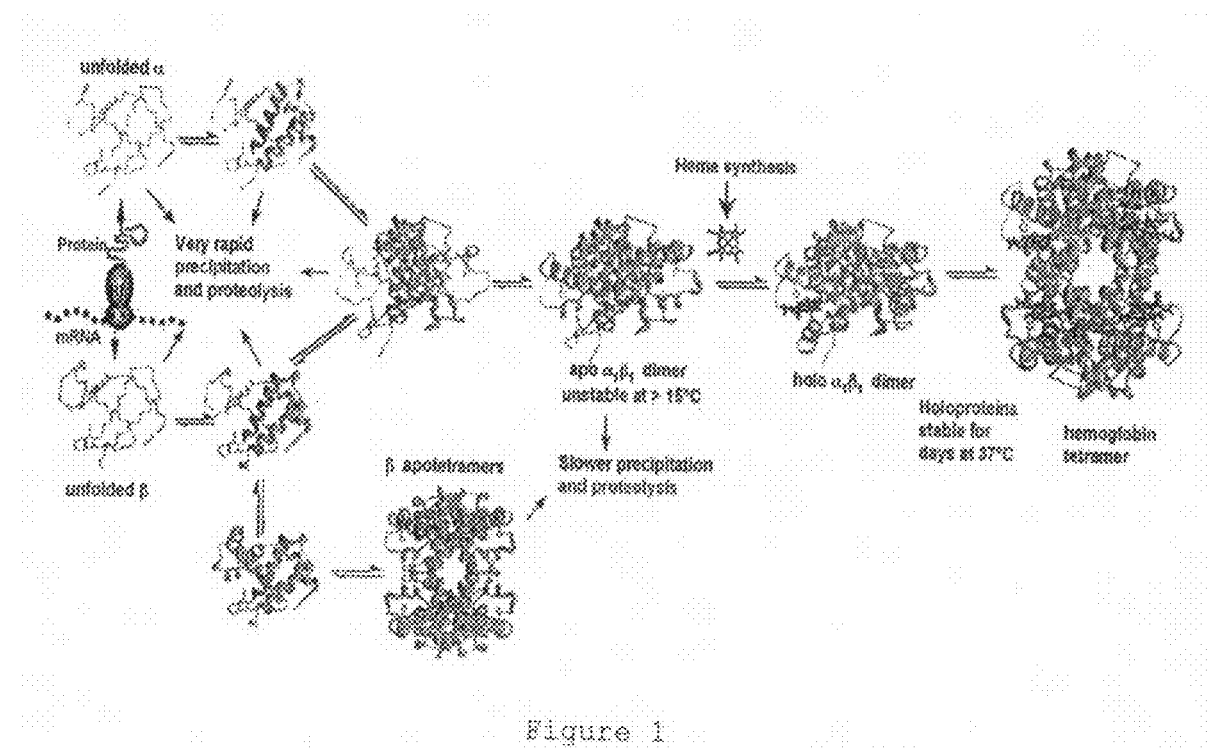
FIG. 1 illustrates a scheme for hemoglobin assembly in both *E. coli*, other microorganisms, and erythroid cells.

The present disclosure relates, in some embodiments, modified forms of hemoglobin and/or myoglobin (e.g., apohemoglobin) and/or methods for producing modified forms of hemoglobin and/or myoglobin (e.g., apohemoglobin). Modified forms of hemoglobin and/or myoglobin (e.g., apohemoglobin) may have improved stability and/or may be suitable for use in blood substitutes. In some embodiments, methods of producing modified forms of hemoglobin and/or apohemoglobin may be produced may result in better yields (e.g., more protein is produced, more of protein produced is functional, and/or protein is produced more cost effectively).

In some embodiments of the disclosure, modified forms of hemoglobin and/or myoglobin (e.g., apohemoglobin) may be administered to a subject. For example, an amount sufficient to improve oxygen delivery may be administered to a subject in conjunction with a blood substitute. Subjects may include humans and non-human mammals. In some embodiments, administration of modified forms of hemoglobin and/or myoglobin (e.g., apohemoglobin) may be associated with little or mo hypertensive side effects relative to administration of corresponding unmodified forms.

According to one example embodiment, the disclosure relates to recombinant adult human apohemoglobin (apo-rHb) in which the stability has been increased by replacement of at least one amino acid with a counterpart from sperm whale α hemoglobin or β hemoglobin or human fetal γ hemoglobin. This mutated apo-rHB may be more stable and/or give higher production yields than unmutated adult human apo-rHb. Some apo-rHb of the present disclosure may be used as part of a blood substitute.

In specific embodiments, more stable human α and β globins may be constructed by modification (e.g., mutation) of adult human rHb that are based on the naturally occurring amino acids found in adult hemoglobins of sperm whales (SW Hb) (and other deep diving mammals) and replacements found in human fetal hemoglobin (HbF). Both SW Hb and HbF are much more resistant to denaturation than native adult human hemoglobin (HbA). Other deep diving mammals may exhibit similar resistance. Additionally, the fetal form of hemoglobin in these mammals may provide even greater resistance to degradation. Resistance to unfolding, degradation, and precipitation may increase production yields in E. coli and other microorganisms, including other bacteria and yeasts, and in animal erythroid cells, such as mammalian erythroid cells.

Based on studies with Mb, enhancement of degradation resistance of heme-free (apo) globin increases the level of production of intact protein by 50 to 100% in E. coli. A similar enhancement of expression level by stabilizing the subunits and interfaces of recombinant hemoglobin may make its production in E. coli not only feasible but also profitable. In some example embodiments, the production of intact, usable rHb may be increased from the current level of 5-10% of E. coli total soluble protein to 30% or more.

Thus, example embodiments of the present disclosure relate to rHb production cells, tissues, or animals in which apo-rHb contains at least one amino acid mutation in the adult human α or β hemoglobin subunit introduced from a sperm whale or deep diving mammal hemoglobin or human fetal hemoglobin, such that the mutated apo-rHb may be more resistant to denaturation and thus may be more stable than unmutated adult human rHb.

Other example embodiments may relate to nucleic acids that encode mutated apo-rHb. These embodiments may also encode at least two different hemoglobin subunits for co-expression in the same cell to produce apo-rHb. Still other example embodiments relate to systems including cells, such as E. coli cells, other microorganisms, or animal erythroid cells, for production of a more degradation-resistant mutated apo-rHb. These systems may also exhibit increased rHb production and fewer degradation products when compared with similar systems for production of unmutated adult human apo-rHb. Other example embodiments relate to methods of making the above cells and nucleic acids as well as to methods of producing mutated apo-rHb.

The present disclosure, according to some example embodiments, may be used in conjunction with existing rHb technologies. For example, it may be used in connection with two co-filed applications U.S. provisional patent application Ser. Nos. 60/610,110 and 60/610,109, as well as U.S. Pat. Nos. 6,455,676; 6,204,009; 6,114,505; 6,022,849; and U.S. patent application publication No. 2003 0017537.

The following discussion relates to specific example embodiments of the disclosure.

The assembly of hemoglobin in either bacteria or in animal erythroid cells is a complex process involving ribosomal synthesis of two different protein chains or subunits (α, 141 amino acids and β, 146 amino acids). The newly synthesized α and β subunits do not appear to have any well-formed structure in the absence of a partner and first assemble to form an $\alpha_1\beta_1$ dimer, which itself is also very unstable (apo $\alpha_1\beta_1$ dimer in FIG. 1, where the suffix apo means no heme is bound and the protein has no "red" color). Only after heme (iron containing red pigment) is bound is the protein stabilized and resistant to degradation. Hemoglobin synthesis in bacteria may be limited by the availability of heme, and as a result, newly formed α and β proteins that are unable to find heme may tend to precipitate or be degraded by bacterial enzymes, particularly α subunits.

Figure 2:
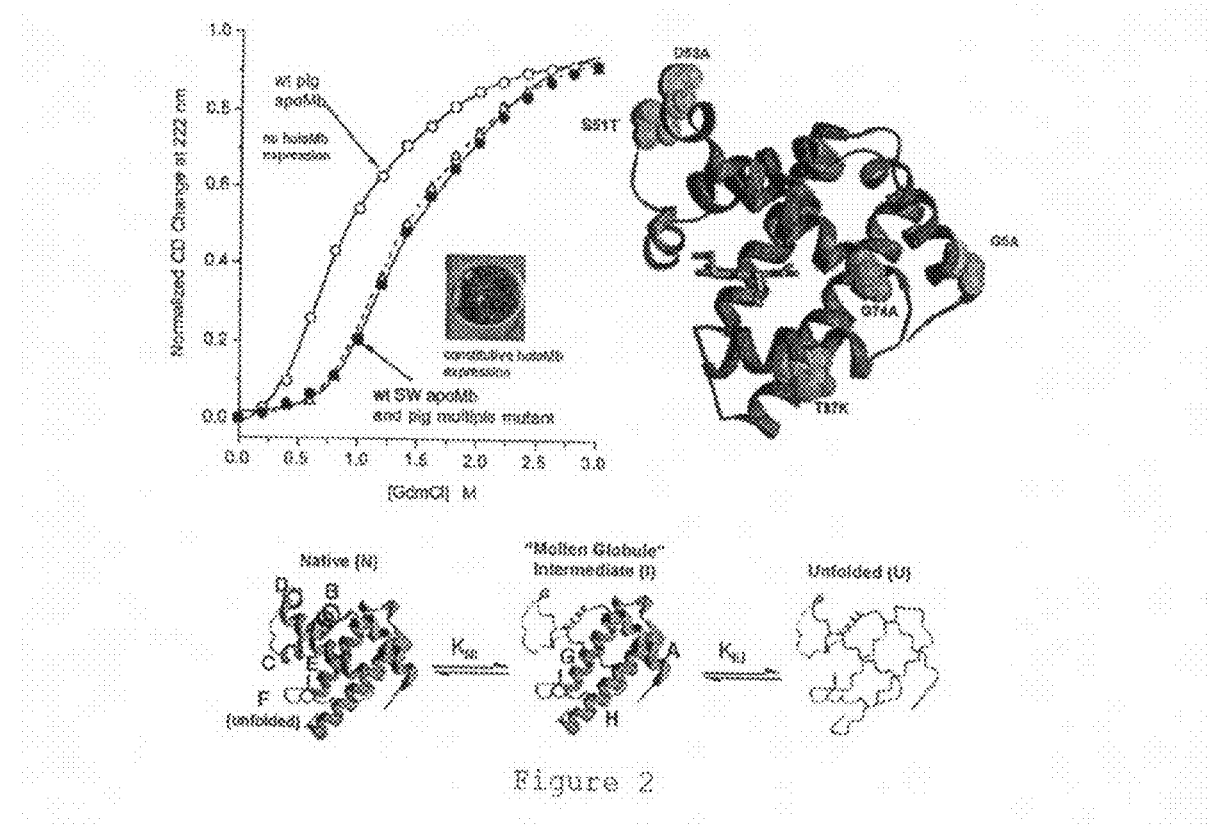
FIG. 2 illustrates the differences in stability of sperm whale and pig apoMb.

Apomyoglobins from deep diving whales are significantly more resistance to denaturation by chemical agents (i.e., guanidinium chloride, urea) than those from the terrestrial or surface swimming mammals, and these proteins may be easily expressed as intact myoglobins in E. coli (FIG. 2). There may be significant selective pressure for increased resistance of Mb to denaturation during the sustained hypoxic and acidotic conditions that occur in whale skeletal muscles during deep and prolonged dives (Zapol, W. M. et al., (1979) *J Appl Physiol* 47, 968-973; Snyder, G. K. (1983) *Respir Physiol.* 54, 269-294; Kooyman, G. L. et al., (1998) *Annu Rev Physiol* 60, 19-32; Tang, Q. et al. (1998) *Biochemistry* 37, 7047-7056)).

As shown in FIG. 2, CD titration curves are shown in the left panel for unfolding of wild-type pig apoMb (open circles), wild-type sperm whale apoMb (filled circles), and pig apoMb with five replacements based on the sequence of the sperm whale protein: G5A/S51T/D53A/G74A/T87K (open triangles) in the titration curve. The two step apoglobin unfolding mechanism is shown at the bottom of the figure (Barrick, D. et al., (1993) *Biochemistry* 32, 3790-3796; Eliezer, D. et al. (1997) *FEBS Lett* 417, 92-96). The thickness of the ribbons indicates the amount of helical structure. Native apomyoglobin (N) retains most of the secondary and tertiary structure present in holomyoglobin except for the F helix. Addition of denaturant unfolds the B, C. D, and E helices to give a molten globule intermediate (I) composed of folded A, G. and H helices. Further addition of denaturant results in the completely unfolded state (U). The spheres in the RIBBONS drawing show the location of the mutated residues. The solid and dashed lines represent global fits to the observed CD and fluorescence changes as described in Scott et al (Scott, E. et al. (2000) *J Biol Chem* 275, 27129-27136).

Apoglobin stability correlates quantitatively with expression, the yield of myoglobin production in vivo with the apoglobin stabilities of ≧35 different mutants that were designed to have widely different heme binding and protein folding properties was measured. (See FIG. 3.) Thus, apoglobin stability has been shown quantitatively to be a major limiting factor in the production of intact heme proteins in E. coli using recombinant myoglobin as a model system (Scott, E. E. et al. (2000) *J Biol Chem* 275, 27129-27136; Smith, L. P. (2003) PhD Dissertation Biochemistry & Cell Biology, Rice University Houston, Tex.; and Olson, J. S. et al. (1997) *Artificial Cells, Blood Substitutes, and Immobilization Biotechnology* 25, 227-241).

In FIG. 3A, the top graph shows the raw absorbance data for a typical assay of E. coli cells expressing wild-type sperm whale myoglobin. For these assays 5 ml cultures were grown overnight using the constitutive expression system of Springer and Sligar (Springer, B. A. et al. (1987) *PNAS* 84, 8961-8965; Olson, J. S. et al. (1997) *Artificial Cells, Blood Substitutes, and Immobilization Biotechnology* 25, 227-241; Smith, L. P. (2003) PhD Dissertation Biochemistry & Cell Biology, Rice University Houston, Tex.). The cells were spun down and resuspended to an $OD_{600\ nm}$ of 0.5 to normalize the number of cells in each assay. The suspensions were flushed with 1 atm of CO and reduced with a small amount of dithionite. Visible spectra were recorded from 600 to ~350 nm and the derivative spectra were calculated numerically as shown. The ratio of the peak to trough absorbance derivative signal for mutant Mb was divided by that for wild-type Mb to obtain relative expression yield used in Also in FIG. 3A, the bottom graph shows the free CO-heme has a broad Soret absorbance band at 412 nm, readily oxidizes to 4-coordinate hemin with a very broad peak at ~380 nm, and does not interfere with the HbCO derivative spectrum (Looker, D. et al. (1994) *Methods Enzymol* 231, 364-374). The peak to trough difference at ~420 nm was used as a measure of holoMb expression level.

The unfolding constant, $K_{NU}$, represents the ratio of denatured unfolded state (U) to the native folded state (N) and can be obtained from titrations with a highly soluble denaturant like guanidinium chloride (GdmCl) or urea which facilitates the N to U reaction. The reciprocal of this value is the folding constant, $K_{UN}=1/K_{NU}$, which indicates how stable the apoglobin is. It is the equilibrium constant for the U to N reaction. For example, wild-type sperm whale myoglobin has $K_{UN}\approx12,000$ so that at equilibrium 12,000 molecules are folded and 1 is unfolded at room temperature. This number is often expressed on a logarithmic scale as $\log K_{UN}$ or from the experimentally determined unfolding constant, $-\log K_{NU}$, for which the negative sign indicates inversion of the constant. The large and more positive the value of $-\log K_{NU}$, the more stable the protein. Thus in FIG. 3B, the points at $-\log K_{NU}$ values equal to +6, indicate a folding constant of 1,000,000 and very stable protein structures which correlate with high levels of expression in *E. coli*.

FIG. 3B shows that apoglobin stability is necessary, but not always sufficient, to achieve high production yields. For example, there are two major apoMb outliers below the lower 90% regression line, indicating that these proteins have reasonable folding constants but express poorly, perhaps due to higher rates of proteolytic degradation and aggregation. In contrast, there are no outliers above the upper dashed line, indicating that no unstable apoMbs express well. Thus, stable apoglobin structures may be required for good production in *E. coli*.

In FIG. 3B, the correlation explains 52% of the total variance and has a p value of 0.0000009. The linear regression between these two parameters is $\log(\text{expression})=-1.26+0.27^*(-\log K_{NU})$. The dashed lines encompass 90% of the data points and are +/−0.42 from the regression line (Smith, L. P. (2003) Biochemistry & Cell Biology, Rice University Houston, Tex.).

Accordingly, Without being limited to any particular mechanism of action or theory, some example embodiments of the present disclosure relate to the creation of more stable α and β subunits that may have strengthened tertiary structures and interactions in the $\alpha_1\beta_1$ interface. For example, dimers may be more resistant to degradation and precipitation while waiting for heme insertion. In some specific example embodiments, amino acid substitutions may include, without limitation, the example substitutions shown in Table 1.

TABLE 1

| Purpose | Mutations (Residues are defined by their helical position, i.e., GlyA13 is at the 13th position of the A helix.) | |
| --- | --- | --- |
| 1. Stabilize the folded state of human apoglobin using mutations based on sequence comparisons with sperm whale Hb. | α GlyA13→Ala(Ser) α GlyB3→Ala (Asp, Glu, Asn) α CE corner mutations α CysG11→Ser, Thr, Val | β GlyA13→Ala(Ser) β ProD2→Ala β GlyD7→Lys β GlyE13→Ala (Thr, Asp) β CysG14→Val, Thr, Ser, Ile β ProH3→Glu, Ala (Gln) |
| 2. Strengthen the $\alpha_1\beta_1$ interface with mutations based on comparisons between the sequences of adult β chains and fetal γ chains. | | β CysG14→Thr β HisG18→Ile(Leu, Ala) β ProH3→Glu β TyrH8→Trp(Leu) β ValH11→Met(Leu, Phe) |

As shown in Table 1, the first set of mutations are designed to increase the stability of the individual subunits based on sequence comparisons between sperm whale and human hemoglobin. This first strategy is based on the assumption that sperm whale hemoglobin is under selective pressure to be more resistant to denaturation.

The second set is designed to strengthen the $\alpha_1\beta_1$ interface based on comparisons between adult β hemoglobin and fetal γ hemoglobin. This strategy is based on the observation that fetal hemoglobin is significantly more resistant to both acid and alkaline denaturation (Bunn, H. F. et al. (1986) *Hemoglobin: Molecular, Genetic, and Clinical Aspects*, W. B. Saunders, Philadelphia). The rate of dissociation of $\alpha_1\beta_1$ dimers may be at least 3-fold smaller than that of $\alpha_1\beta_1$ dimers and the rate of assembly of holo-α chains with holo-β chains containing G and H helical substitutions based on γ chains may have significantly higher bimolecular rates of dimer formation (Mrabet, N. T. et al. (1986) *J Biol Chem* 261, 1111-1115; McDonald, M. J. et al. (1987) *J Biol Chem* 262, 5951-5956; Adachi, K. et al. (2001) *Biochem Biophys Res Commun* 289, 75-79; Adachi, K. et al (2003) *Biochemistry* 42, 10252-10259; Joshi, A. A. (1994) *J Biol Chem* 269, 8549-8553). The replacements found in γ chains significantly stabilize the $\alpha_1\beta_1$ dimer interface and increase resistance to apo-dimer unfolding, which, when used in the context of the present disclosure, may enhance expression in a microorganism, such as *E. coli*.

Figure 3:
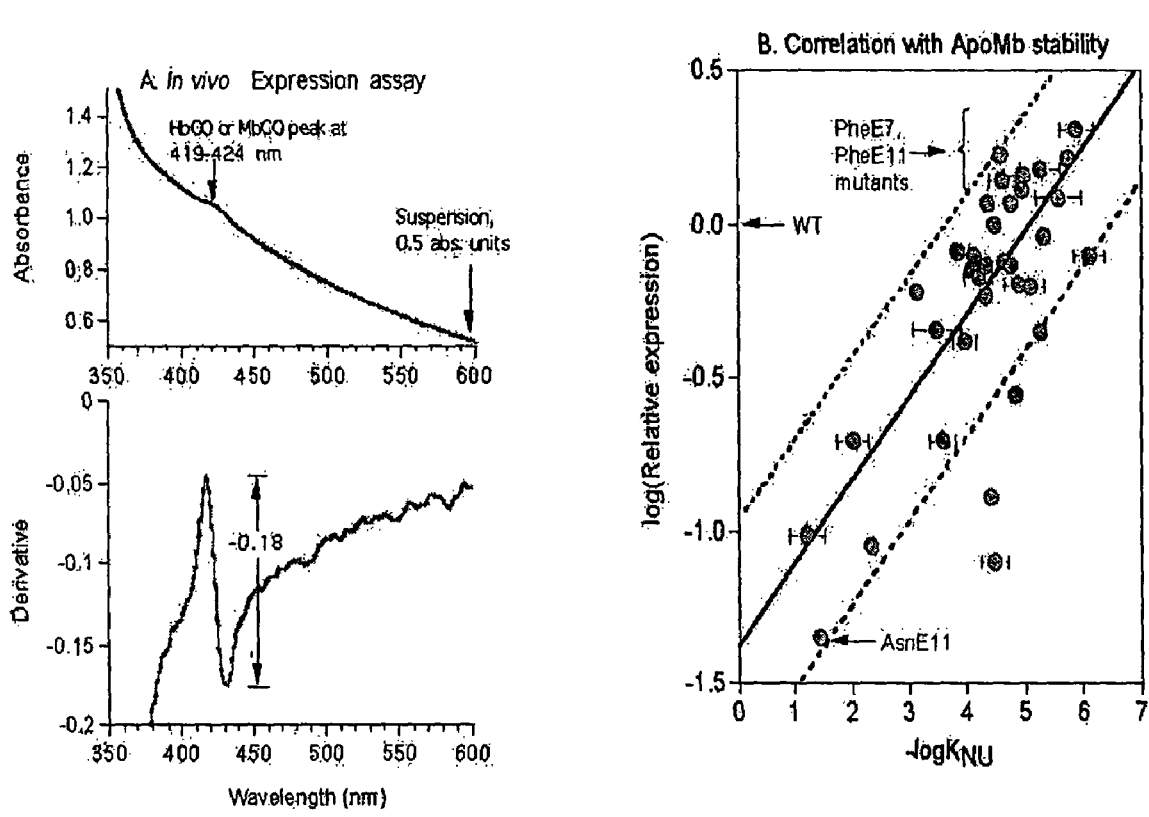
FIG. 3 illustrates in vivo expression of holomyoglobin (holoMb) and correlations with the rates of and apomyoglobin (apoMb) stability.

Over ten years ago, it was discovered that sperm whale apomyoglobin is 20 to 100 times more resistant to GdmCl-induced denaturation than most other mammalian apoMbs (FIGS. 2 and 3, and (Scott, E. E. (2000) *J Biol Chem* 275, 27129-27136; Hargrove, M. S. et al. (1994) *Biochemistry* 33, 11767-11775)). This observation has been discussed anecdotally in the literature and accounts for why sperm whale apoMb was chosen for detailed unfolding studies (Hughson, F. M. et al. (1990) *Science* 249, 1544-1548; Nishimura, C. et al. (2003) *J Mol Biol* 334, 293-307; Nishimura, C. et al. (2000) *Nat Struct Biol* 7, 679-686; Garcia, C. et al. (2000) *Biochemistry* 39, 11227-11237; Eliezer, D. et al. (2000) *Biochemistry* 39, 2894-2901). Sperm whale holomyoglobin can be expressed constitutively in large amounts in *E. coli* without adding heme and without producing large amounts of unfolded apoprotein in inclusion bodies. In contrast, pig and human myoglobin generally cannot be expressed readily as holoproteins without adding hemin (Varadarajan, R. et al. (1985) *PNAS* 82, 5681-5684; Dodson, G. et al. (1988) *Protein Eng* 2, 233-237; Springer, B. A. et al. (1987) *PNAS* 84, 8961-8965; Lloyd, E. et al. (1994) *FEBS Lett* 340, 281-286). The underlying physiological cause of these differences was discovered in a study of the unfolding properties of 13 different mammalian Mbs (Scott, E. E. et al. (2000) *J Biol Chem* 275, 27129-27136). ApoMbs from deep diving whales are significantly more stable than those from the terrestrial or surface swimming mammals that were examined. These results indicate, among other things, that there is significant selective pressure for increased resistance of Mb to denaturation during the sustained hypoxic and acidotic conditions that occur in whale skeletal muscles during deep and prolonged dives (Zapol, W. M. et al. (1979) *J Appl Physiol* 47, 968-973; Snyder, G. K. (1983) *Respir Physiol* 54, 269-294; Kooyman, G. L. et al. (1998) *Annu Rev Physiol* 60, 19-32; Tang, Q. et al. (1998) *Biochemistry* 37, 7047-7056).

GdmCl-induced unfolding curves for 28 different apoMbs were analyzed in terms of the two-step, three-state mechanism first described by Barrick, Baldwin, and Wright (FIG. 2, and Barrick, D. et al. (1993) *Biochemistry* 32, 3790-3796; and Hughson, F. M. et al. (1990) Science 249, 1544-1548), using algorithms devised by Eftink's group to analyze combined CD and fluorescence data (Ramsay, G. et al. (1995) *Biophys J,* 69, 701-707). The fitted values of $K_{NI}$ and $K_{IU}$ represent equilibrium constants for the native (N) to intermediate (I)

and intermediate (I) to unfolded (U) transitions in the absence of denaturant. NMR and mutagenesis studies have shown that the first transition involves "melting" of the heme pocket, with little change in secondary structure of the A, G, and H helical core (Hughson, F. M. et al. (1990) *Science* 249, 1544-1548; Nishimura, C. et al. (2003) *J Mol Biol* 334, 293-307; Garcia, C. et al. (2000) *Biochemistry* 39, 11227-11237; Eliezer, D. et al. (1998) *Nat Struct Biol* 5, 148-155). Higher concentrations of GdmCl are required to melt this more stable region in the second transition. The overall stability of native apoMb can be measured empirically as the concentration of GdmCl that causes 50% of the overall CD change, [GdmCl]$_{midpoint}$ or as $logK_{UN}$, which is calculated as $-log(K_{NU})$.

Comparisons of the amino acid sequences of pig and sperm whale myoglobin suggest several substitutions that might account for the differences in stability. As shown in FIG. 2, five replacements are sufficient to increase the stability of pig apoMb to that of wild-type sperm whale apoMb. The three alanine mutations, G5A, D53A, and G74A, appear to stabilize the native state by elongating and strengthening the A, D, and E helices. Scott et al.'s results, however, do not show that mutation of human hemoglobin will produce useful, stabilizing changes, which sites should be mutated, or that any mutants will actually increase production yield in bacteria, such as *E. coli*.

Figure 4A:
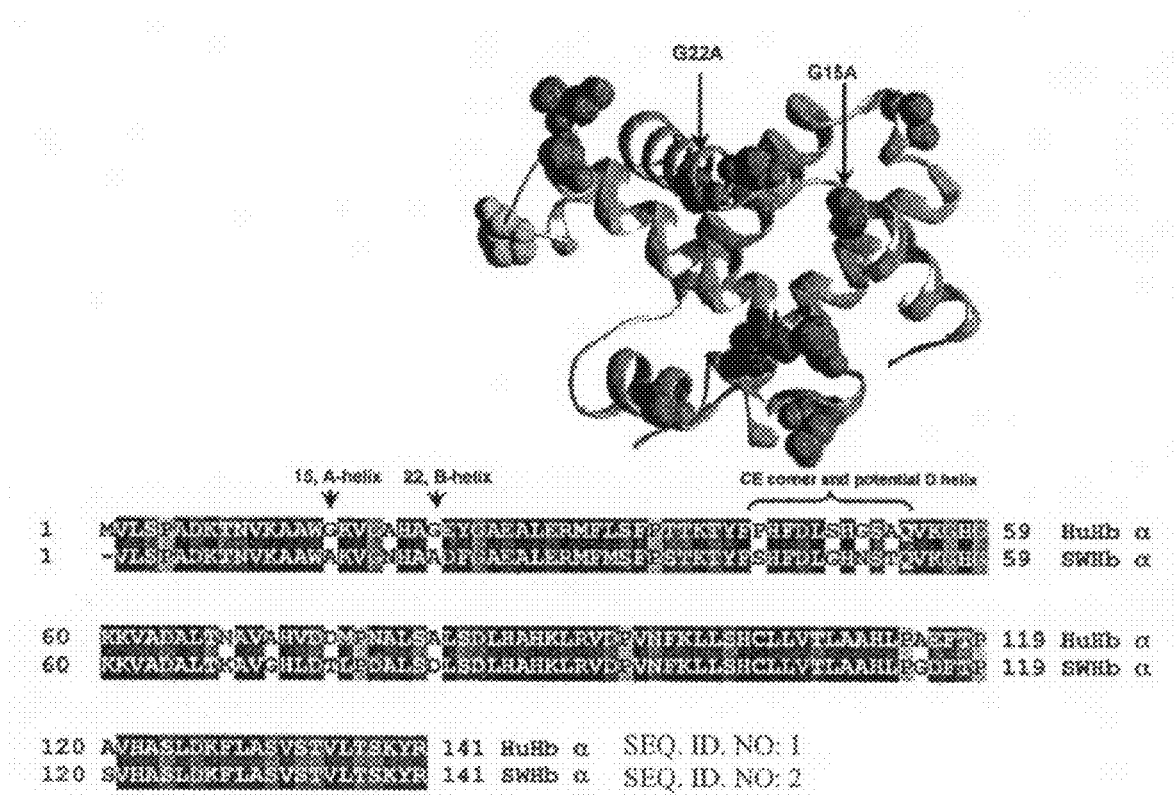
FIGS. 4A and 4B provide a sequence comparison between human and sperm whale α and β hemoglobin genes. Arrows indicate possible mutations to stabilize the human subunits.
Figure 4B:
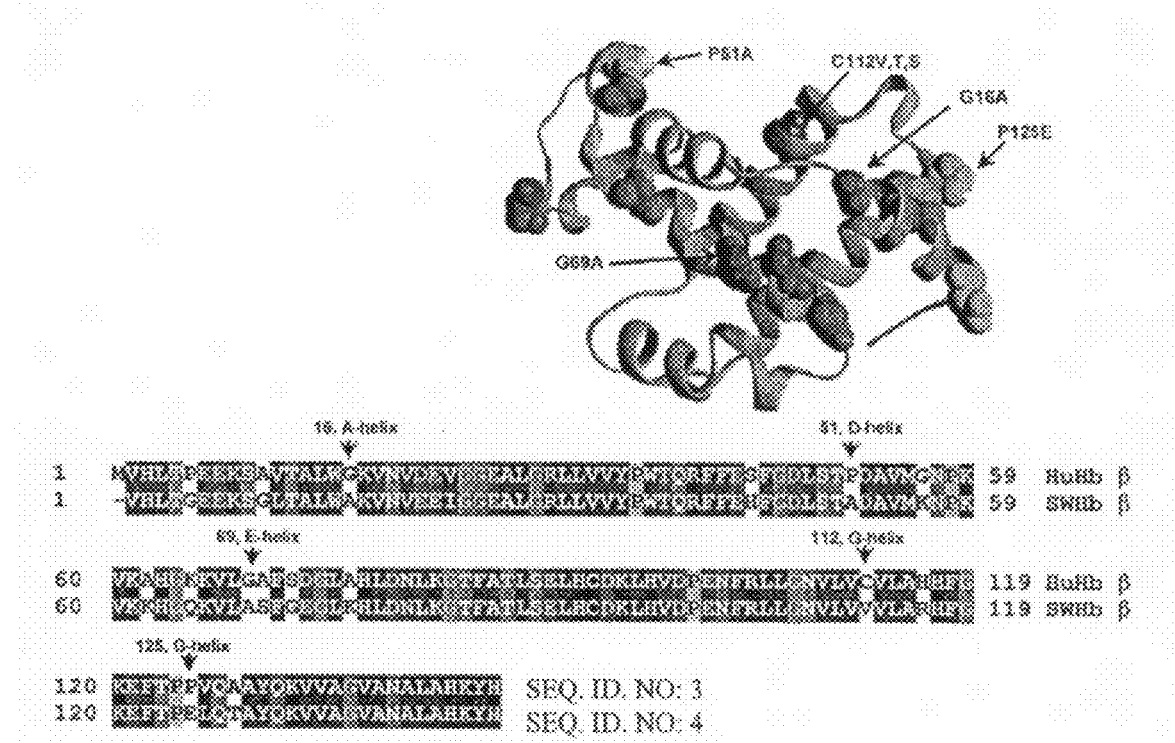
Figures 4C, 4D:
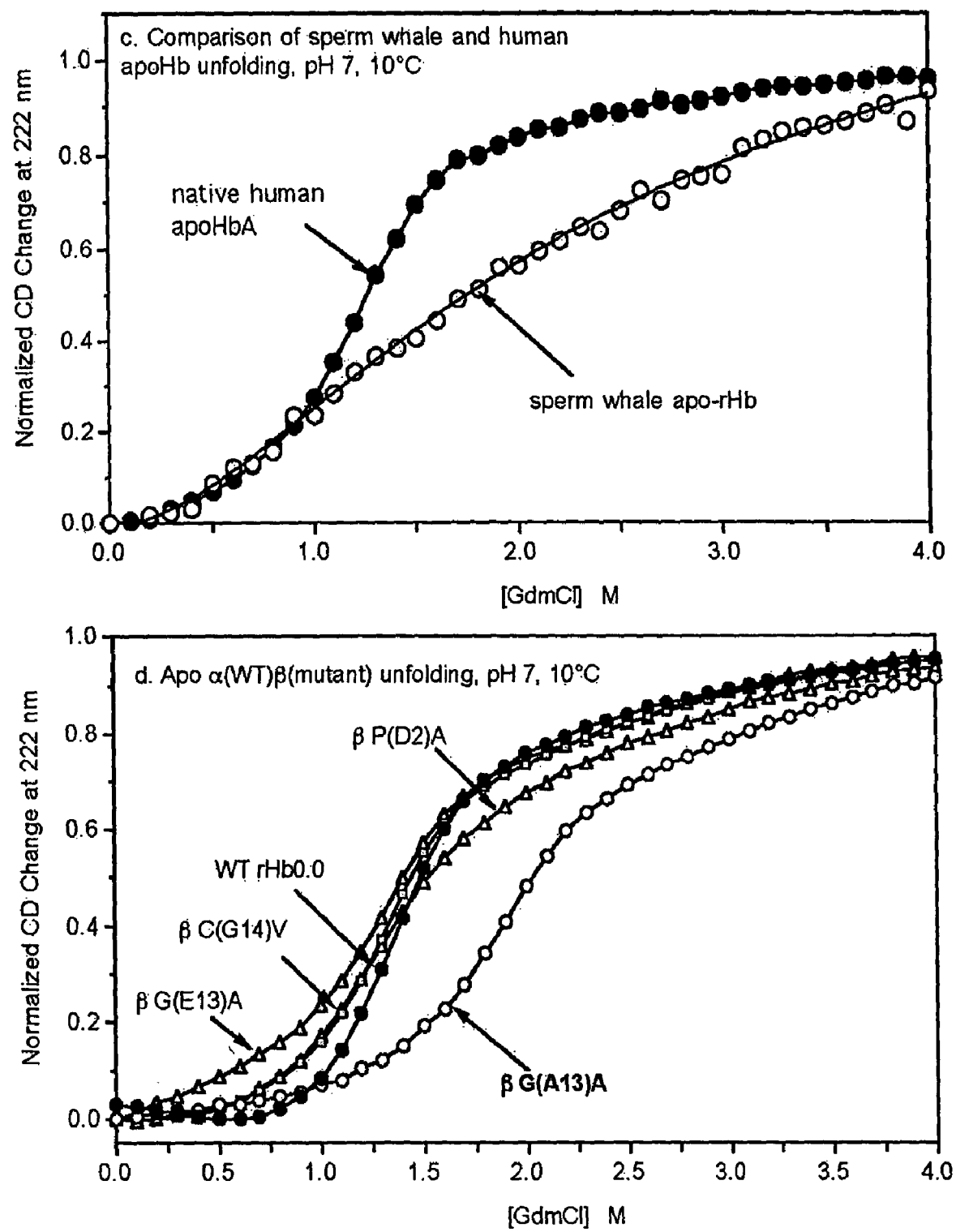
FIG. 4C provides a comparison of the GdmCl unfolding curves of native human and recombinant sperm whale apoHbs. The broad sperm whale apoHb curve is completely reversible and independent of total protein concentration in the range 2.5 to 10 μM (data not shown).
FIG. 4D illustrates the unfolding curves for four α(wild-type)β (mutant) hybrid human apoHbs. The β(G(A13)A) mutation causes a marked increase in stability, with $[GdmCl]_{midpoint}$ increasing from ~1.4 to 2.1 M.

Sperm whale and human hemoglobin subunits may be compared and used to selectively mutate human hemoglobin subunits based on the assumption that sperm whale hemoglobin will be more resistant to unfolding as a result of the same selective pressure that caused whale Mb to be more stable. Thus, a comparison between the primary sequences of SW and human $\beta$ and $\alpha$ chains was made and mutations were selected based on increases in helix propensities. Synthetic sperm whale $\alpha$ and $\beta$ genes based on the naturally occurring sequence were constructed and expressed and the recombinant whale hemoglobin was purified. The sequence comparisons, proposed mutations, and results with recombinant SW apoHb and four human $\beta$ chain mutants are shown in FIG. 4 and Table 1. As shown in FIG. 4C, sperm whale apoHb is more resistant to unfolding induced by GdmCl than the human apoprotein at high denaturant concentrations and exhibits a very broad CD transition, suggesting that the whale apoHb has more stable folding intermediates than the human protein.

Figure 5:
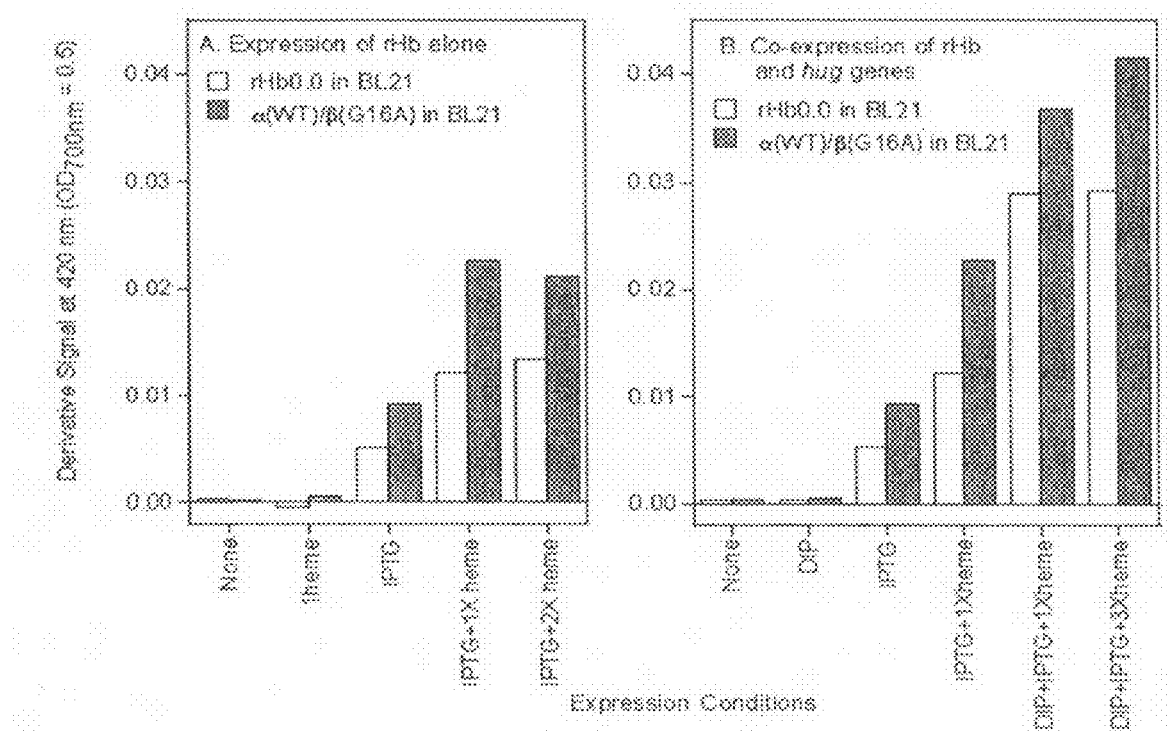
FIG. 5 illustrates measurements of holo-rHb0.0 and holo-rHb(α(wt)/β(G16A)) production in *E. coli* BL21 cells with and without co-expression of the hug genes on pHUG21.1.

Some $\alpha$ hemoglobin mutations of some example embodiments of the present disclosure include, but are not limited to, Gly15 to Ala and Gly22 to Ala. These specific replacements were chosen because they suggest that the carboxy-terminus of the A helix and the amino-terminus of the B helix are stabilized by alanine side chains in whale $\alpha$ subunits. The same Gly to Ala mutation at the $\beta$ hemoglobin A13 helical position causes a marked enhancement in human apoHb stability ($\beta$ G(A13)A curve in FIG. 4D). $\beta$ subunit mutations of other example embodiments of the present disclosure are shown in FIG. 4B, and four of these replacements have been made in $\alpha$(wild-type)$\beta$(mutant) rHb tetramers. The $\beta$ Gly16 to Ala mutation at the A13 helical position is very successful in enhancing the resistant of human apoHb to unfolding. The shift in midpoint GdmCl concentration for $\beta$ G16A apoHb suggests an ~50-fold increase in overall stability, and remarkably, this human rHb single mutant appears to be more stable than sperm whale hemoglobin itself. As shown in FIG. 5, the measured expression level of the $\beta$ Gly(A13)Ala mutant is ~2 times greater than that of the simple wild-type rHb0.0. This two-fold enhancement of expression occurs in the absence and presence of heme (FIG. 5A). Co-expression of the heme ultilization (hug) genes (+DIP) enhances the production of both proteins significantly, but again the more stable $\beta$ (Gly16 (A13)Ala) mutant still expresses to a much higher level (FIG. 5B). These results demonstrate, among other things, that enhanced resistance to denaturation does result in higher expression levels.

Briefly, in FIG. 5 *E. coli* BL21(D3) cells were co-transformed with PHUG 21.1/prHb0.0 plasmids and maintained on agar plates containing tetracycline and chloramphenicol. Tubes containing 5 ml of LB broth were inoculated and then grown overnight at 37° C. Various additions were made to the cultures including IPTG, heme (increments of 10 µM total=1X), and 2,2-dipyridine, DIP (63 µM total), and the cultures were incubated at 37° C. for another 16 hours. Then the cells were pelleted, resuspended to 0.5 absorbance units at 700 nm in Tris buffer, pH 7.5, and equilibrated with 1 atm of CO for 15 minutes to ensure HbCO formation and no further cell growth. Spectra of these samples were recorded and first derivatives of the observed spectra were calculated. No rHbCO is detected in the absence of IPTG induction, regardless of whether heme or DIP is added to the cultures.

Bunn, McDonald, Adachi, and co-workers have shown that the rate of dissociation of $\alpha_1\beta_1$ dimers is at least 3-fold smaller than that of $\alpha_1\beta_1$ dimers, and that the rate of assembly of holo-$\alpha$ chains with holo-$\beta$ chains containing G and H helical substitutions based on $\gamma$ chains can have significantly higher bimolecular rates of dimer formation (Mrabet, N. T. et al. (1986) *J Bioi Chem* 261, 1111-1115; Joshi, A. A. et al. (1994) *J Bioi Chem* 269, 8549-8553; Adachi, K. et al. (2001) *Biochem Biophys Res Commun* 289, 75-79; and Adachi, K. et al. (2003) *Biochemistry* 42, 10252-10259).

Figure 6:
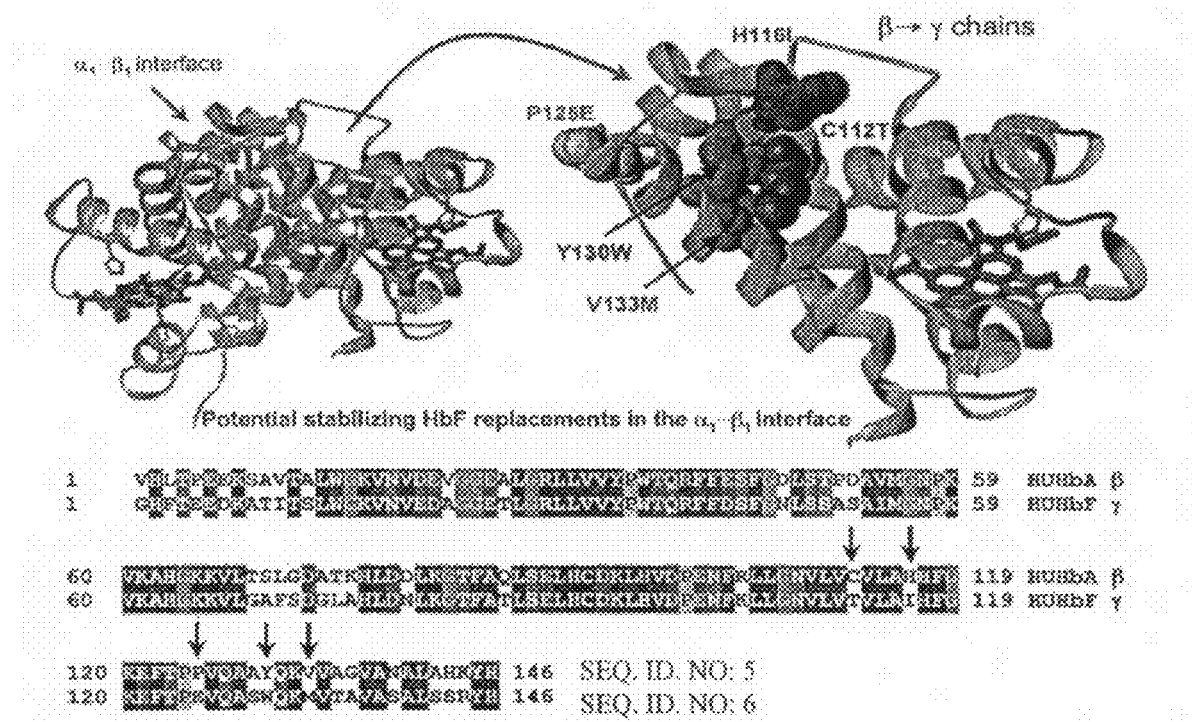
FIG. 6 illustrates a sequence comparison between human β and γ chains and proposed mutations in the $\alpha_1\beta_1$ interface.

As mentioned above, the sequences of human adult $\beta$ chains may be compared with the human $\gamma$ chains from fetal hemoglobin, which is known to be more stable (FIG. 6). A similar approach may be used to exam fetal whale hemoglobin, or fetal hemoglobins from other organisms. The highlighted replacements were selected to stabilize the $\alpha_1\beta_1$ interface, partially based on mutagenesis and kinetic studies of subunit assembly and dissociation by Bunn, McDonald, Adachi and co-workers (Mrabet, N. T. et al. (1986) *J Bioi Chem* 261, 1111-1115; McDonald, M. J. et al. (1987) *J Biol Chem* 262, 5951-5956; Adachi, K. et al. (2001) *Biochem Biophys Res Commun* 289, 75-79; Adachi, K. et al. (2003) *Biochemistry* 42, 10252-10259; Joshi, A. A. et al. (1994) *J Bioi Chem* 269, 8549-8553). $\beta$ Cys112 to Ser and Thr mutations increase the rate of formation of holo-dimers and have the advantage of removing a potentially reactive thiol group. The $\beta$ His116 to Ile mutation facilitates subunit assembly by enhancing the apolar surface of the $\alpha_1\beta_1$ interface. The $\beta$ Pro125 to Glu mutation is based on the presence of Glu, Gln, Glu, and Glu at this position in human $\zeta$, $\delta$, $\gamma$, and $\epsilon$ chains, respectively, and removal of a Pro should strengthen the H helix. The remaining $\beta$ Tyr130 to Trp (H8) and Val133 to Met (H11) mutations are partially based on suggestions by Bunn and Forget ((1986) *Hemoglobin: Molecular, Genetic, and Clinical Aspects*, W. B. Saunders, Philadelphia) that these naturally occurring replacements enhance the hydrophobicity of the interior of the $\alpha_1\beta_1$ interface. The corresponding amino acids in human $\alpha$, $\zeta$, and $\epsilon$ chains are Leu, Trp, and Trp, respectively, at the H8 helical position and Phe, Phe, and Leu, respectively, at the H11 position, implying that there may be selection for large apolar residues.

While not meant to be limited by theory, newly translated apoprotein generally should remain in solution and be resistant to proteolysis long enough for heme to be made available by either bacterial synthesis or transport of externally added heme. In this model, there is competition between precipitation and proteolysis of the unfolded states and heme binding to the native state. If the fractions of the unstable I and U states are relatively high and the rate of heme transport and/or synthesis is low, little holoprotein will be expressed. Lucian Smith verified this model using an in vivo assay for holoMb production in *E. coli* and comparing the observed expression levels with the stabilities ($-logK_{NU}$) of the corresponding apoglobin mutants (Smith, L. P. (2003) The Effects of Amino Acid Substitution on Apomyoglobin Stability, Folding Intermediates, and Holoprotein Expression. PhD Dissertation, Biochemistry & Cell Biology, Rice University Houston, Tex.). A similar comparative mutagenesis strategy may be used to enhance the stability and expression of recombinant human hemoglobin.

A simple scheme for the assembly of holohemoglobin tetramers is shown in FIG. 1, which based on heme binding and dissociation experiments (Antonini, E., and Brunori, M. (1971) *Hemoglobin and Myoglobin in their Reactions with Ligands*. Frontiers in Biology (Neuberger, A., and Tatum, E. L., Eds.), 21, North-Holland Publishing Company, Amsterdam; Ascoli, F. et al. (1981) *Methods Enzymol* 76, 72-87; Gibson, Q. H. et al. (1960) *Biochem J* 77, 328-341; Gibson, Q. H. et al. (1963) *J Biol Chem* 238, 1384-1388; Rose, M. Y. et al. (1983) *J Biol Chem* 258, 4298-4303; Hargrove, M. S. et al. (1996) *Biochemistry* 35, 11293-11299; Hargrove, M. S. et al. (1997) *J Biol Chem* 272, 17385-17389; Bunn, H. F. et al. (1986) *J Biol Chem* 243, 465-475), studies of the hydrodynamic and fluorescence properties of apoHb dimers (Oton, J. et al. (1984) *Arch Biochem Biophys* 228, 519-524; Kowalczyk, J. et al. (1983) *Biochemistry* 22, 4805-4809; Chu, A. H. et al. (1979) *J Biol Chem* 254, 3772-3776; Chu, A. H. et al. (1979) *J Biol Chem* 254, 371-376; Sassaroli, M. et al. (1984) *Biochemistry* 23, 2487-2491), and measurements of the rates of dimer and tetramer formation and dissociation (Shaeffer, J. R. et al. (1984) *J Biol Chem* 259, 14544-14547; Mrabet, N. T. et al. (1986) *J Biol Chem* 261, 1111-1115; Mrabet, N. T. et al. (1986) *J Biol Chem* 261, 5222-5228; Moulton, D. P. et al. (1994) *Biochem Biophys Res Commun* 199, 1278-1283; Joshi, A. A. et al. (1994) *J Biol Chem* 269, 8549-8553; McDonald, M. J. et al. (1990) *Biochemistry* 29, 173-178; Ip, S. H. et al. (1977) *J Biol Chem* 252, 82-87). When heme is removed from human Hb, the resultant apoprotein is a dimer with the $\alpha_1\beta_1$ interface still intact. This protein is much less stable than apoMb and rapidly denatures at temperatures $\geq 15°$ C., even at low concentrations; the individual apoHb subunits are even less stable. Apo-α chains do not appear to have any well-formed structure in the absence of a partner β subunit, whereas secondary structure is observed for isolated β apoglobin subunits, which self-assemble into $\beta_4$ units at high concentrations, even in the absence of heme (Oton, J. et al. (1984) *Arch Biochem Biophys* 228, 519-524; O'Malley, S. M. et al. (1994) *J Protein Chem* 13, 561-567; Waks, M. et al. (1973) *J Biol Chem* 248, 6462-6470). By analogy with apoMb, some nucleation of the G and H helical regions likely occurs in the apo-Hb subunits to allow formation of a stable $\alpha_1\beta_1$ dimer interface (FIG. 1). Brunori and co-workers have recently suggested that this type of G and H helical intermediate occurs universally during the folding of all animal globins (Musto, R. et al. (2004) *Biochemistry* 43, 230-236).

Figure 7:
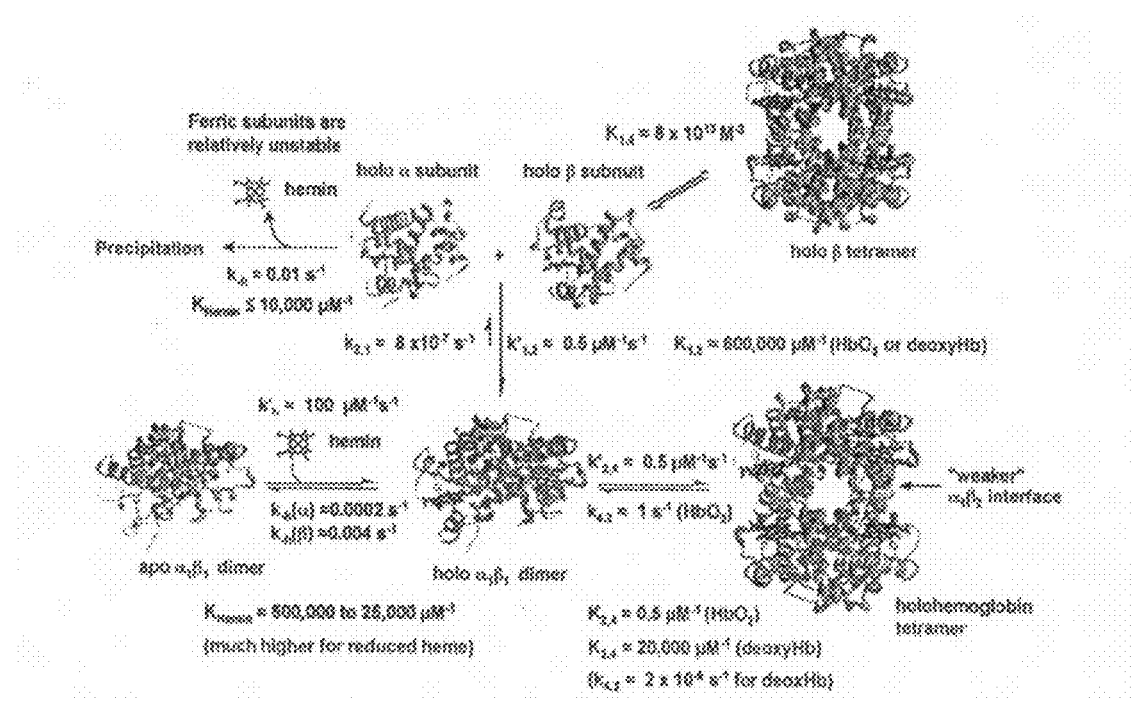
FIG. 7 illustrates the in vitro formation of hemoglobin tetramers starting from apodimers or holomonomers.

Much more is known about the assembly of holohemoglobin dimers and monomers, and a summary is shown in FIG. 7 (Shaeffer, J. R. et al. (1984) *J Biol Chem* 259, 14544-14547; Mrabet, N. T. et al. (1986) *J Biol Chem* 261, 1111-1115; Mrabet, N. T. et al. (1986) *J Biol Chem* 261, 5222-5228; Joshi, A. A. et al. (1994) *J Biol Chem* 269, 8549-8553; Ip, S. H. et al. (1977) *J Biol Chem* 252, 82-87; McGovern, P. et al. (1976) *J Biol Chem* 251, 7871-7879; McDonald, M. J. et al. (1987) *J Biol Chem* 262, 5951-5956; Wiedermann, B. L. et al. (1975) *J Biol Chem* 250, 5273-5275; McDonald, M. J. et al. (1984) *Prog Clin Biol Res* 165, 3-15; Bunn, H. F. et al. (1983) *Nature* 306, 498-500; Vasudevan, G. et al. (1997) *J Biol Chem* 272, 517-524; Yamaguchi, T. et al. (2000) *Biochem Biophys Res Commun* 270, 683-687; Vasudevan, G. et al. (2000) *J Protein Chem* 19, 583-590; Adachi, K. et al. (2001) *Biochem Biophys Res Commun* 289, 75-79; Vasudevan, G. et al. (2002) *Curr Protein Pept Sci* 3, 461-466; Jennings, T. M. et al. (2002) *Biochem Biophys Res Commun* 293, 1354-1357). The initial bimolecular association rate constant for heme binding to apoglobins is large, $\sim 100\ \mu M^{-1}s^{-1}$, relatively independent of protein structure, and effectively irreversible due to extremely low rate constants for heme dissociation (Gibson, Q. H. et al. (1960) *Biochem J* 77, 328-341; Gibson, Q. H. et al. (1963) *J Biol Chem* 238, 1384-1388; Rose, M. Y. et al. (1983) *J Biol Chem* 258, 4298-4303; Hargrove, M. S. et al. (1996) *Biochemistry* 35, 11293-11299; Hargrove, M. S. et al. (1997) *J Biol Chem* 272, 17385-17389; Hargrove, M. S. et al. (1996) *Biochemistry* 35, 11310-11318; Benesch, R. E. et al. (1990) *J Biol Chem* 265, 14881-14885; Gattoni, M. et al. (1996) *J Biol Chem* 271, 10130-10136). The rate constants for holo-monomer to dimer and holo-dimer to tetramer association are about the same, between 0.2 and 0.5 $\mu M^{-1}s^{-1}$, and roughly independent of whether or not $O_2$ is bound to the heme iron. However, the rate of tetramer to dimer dissociation changes almost a million-fold, from $\sim 1\ s^{-1}$ to $2\times 10^{-5}\ S^{-1}$ when $HbO_2$ is deoxygenated (Ip, S. H. et al. (1977) *J Biol Chem* 252, 82-87; Ip, S. H. et al. (1976) *Biochemistry* 15, 654-660) and is the underlying cause of cooperative $O_2$ binding (Perutz, M. F. (1970) *Nature* 228, 726-739; Perutz, M. F. (1990) *Annual Review of Physiology* 52, 1-25; Edelstein, S. J. (1975) *Annu Rev Biochem* 44, 209-232; Ackers, G. K. (1980) *Biophys J* 32, 331-346; Ackers, G. K. (1998) *Adv Protein Chem* 51, 185-253). In contrast, the rate of holo-$\alpha_1\beta_1$ dimer dissociation, $k_{2,1} \approx 1\times 10^{-6}\ s^{-1}$, is little affected by $O_2$ binding, but this dimer dissociation rate constant does increase markedly, to $\sim 10^{-4}\ s^{-1}$, in the absence of heme. This 100-fold increase in $k_{2,1}$, coupled with the rapid unfolding of separated apo-subunits, accounts for the instability of human apoHb at room temperature (Mrabet, N. T. et al. (1986) *J Biol Chem* 261, 1111-1115; Moulton, D. P. et al. (1994) *Biochem Biophys Res Commun* 199, 1278-1283).

In FIG. 7, Rate constants for hemin binding to native apohemoglobin (apoHb) dimers and monomers were taken from (Rose, M. Y. et al. (1983) *J Biol Chem* 258, 4298-4303; and Hargrove, M. S. et al. (1997) *J Biol Chem* 272, 17385-17389). Association rate constants for dimer and tetramer formation were taken from (Ip, S. H. et al. (1977) *J Biol Chem* 252, 82-87; McGovern, P. et al. (1976) *J Biol Chem* 251, 7871-7879; McDonald, M. J. et al. (1987) *J Biol Chem* 262, 5951-5956), and the dissociation rate constants from (Ip, S. H. et al. (1977) *J Biol Chem* 252, 82-87). The equilibrium constant for tetramerization of β subunits was taken from (Ip, S. H. et al. (1977) *J Biol Chem* 252, 82-87; McGovern, P. et al. (1976) *J Biol Chem* 251, 7871-7879). At high concentrations, holo-α chains do appear to dimerize, but the physiological relevance of this weak interaction is unclear. In patients with β-thalassemia (lacking β genes), the excess α chains form precipitates (Heinze bodies) in red cells. In contrast, large amounts of stable holo-$\beta_4$ tetramers are seen in red cells of patients with α-thalassemia (lacking α genes) (Bunn, H. F., and Forget, B. G. (1986) *Hemoglobin: Molecular, Genetic, and Clinical Aspects*, W. B. Saunders, Philadelphia).

One example embodiment of the present disclosure thus relates to Hb mutants whose apoglobin subunits are stable at room temperature. Studies of the folding characteristics of apo-α and β chains allow more sophisticated analyses of the overall apoHb unfolding curves. Similarly, a more stable apoHb dimer allows direct comparisons between GdmCl, acid, and thermally induced folding, adding more physiological relevance to stability measurements. In addition to creating a much more stable and highly expressing rHb molecule, some embodiments of the disclosure also focus on doing so without creating antigenic sites and compromising reduced rates of NO scavenging and efficient $O_2$ transport.

Figure 8:
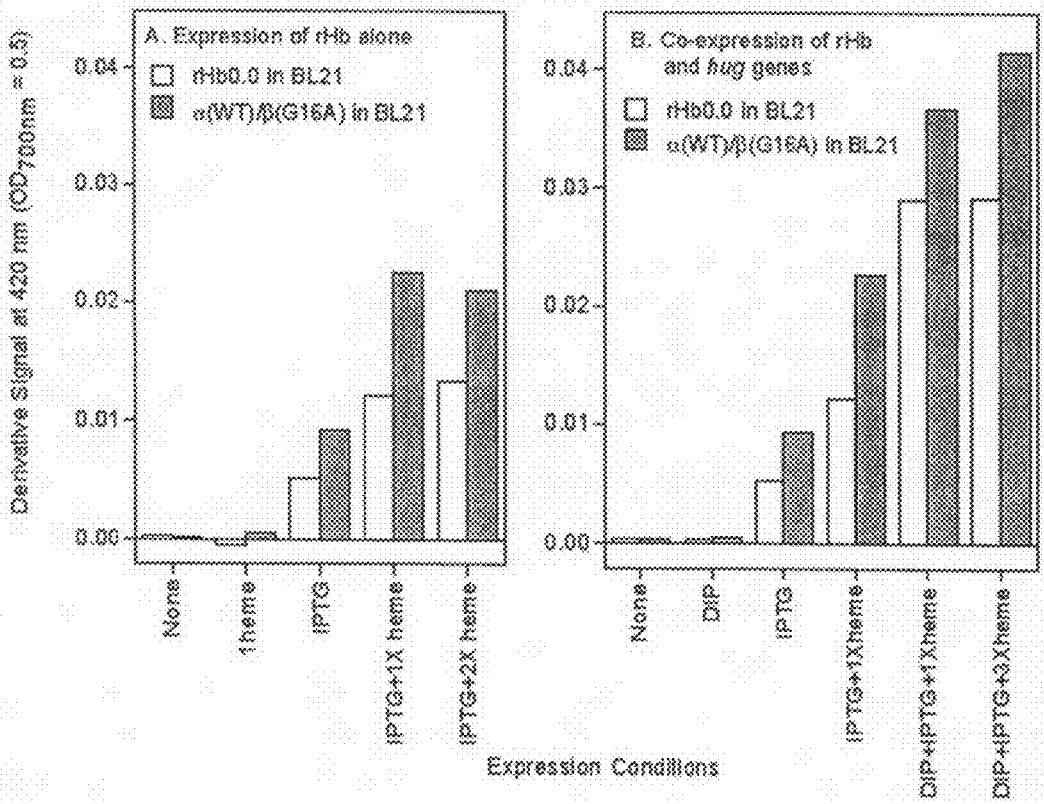
FIG. 8 illustrates measurement of holo-rHb0.0 and holo-rHb(α(wt)/β(G16A)) production in *E. coli* BL21 cells co-transformed with pHUG21.1. The derivative signal was the peak to trough distance in the derivative spectra at 420 nm. Note that almost twice as much of the β(G16A) mutant was expressed compared to wild-type rHb0.0. This two-fold enhancement of expression occurred in the absence and presence of heme (FIG. 8A). Co-expression of the hug genes (+Dip) enhanced the production of both proteins markedly and reduced the differences in the levels between the wild-type and mutant rHbs (FIG. 8B).

Finally, a comparison of the holoprotein yields of wild-type and α((wt)/β(G16A) rHb in small cultures in the absence and presence of heme and heme transport genes, for example, hug genes from *Plesiomonas shigelloides*, is shown in FIG. 8. FIG. 8 confirms that enhancing apohemoglobin stability increases holoprotein expression levels. In the absence of the hug genes, the mutant expression level was roughly twice that of the wild-type protein. This ratio became smaller as heme transport efficiency was increased by the hug transport system, but in all cases, more intact mutant protein was made. Thus, according to some example embodiments of the present disclosure, the mutant α and β hemoglobin may be usefully combined with other methods of increasing hemoglobin production, such as co-expression of heme transport genes to increase hemin uptake.

SEQUENCE LISTING

<160> NUMBER OF SEQ ID NOS: 6

<210> SEQ ID NO 1
<211> LENGTH: 142
<212> TYPE: PRT
<213> ORGANISM: HUMAN HB ALPHA CHAIN

<400> SEQUENCE: 1

```
MET VAL LEU SER PRO ALA ASP LYS THR ASN VAL LYS ALA ALA TRP GLY
1               5                   10                  15

LYS VAL GLY ALA HIS ALA GLY GLU TYR GLY ALA GLU ALA LEU GLU ARG
            20                  25                  30

MET PHE LEU SER PHE PRO THR THR LYS THR TYR PHE PRO HIS PHE ASP
        35                  40                  45

LEU SER HIS GLY SER ALA GLN VAL LYS GLY HIS GLY LYS LYS VAL ALA
    50                  55                  60

ASP ALA LEU THR ASN ALA VAL ALA HIS VAL ASP ASP MET PRO ASN ALA
65                  70                  75                  80

LEU SER ALA LEU SER ASP LEU HIS ALA HIS LYS LEU ARG VAL ASP PRO
                85                  90                  95

VAL ASN PHE LYS LEU LEU SER HIS CYS LEU LEU VAL THR LEU ALA ALA
            100                 105                 110

HIS LEU PRO ALA GLU PHE THR PRO ALA VAL HIS ALA SER LEU ASP LYS
        115                 120                 125

PHE LEU ALA SER VAL SER THR VAL LEU THR SER LYS TYR ARG
    130                 135                 140
```

<210> SEQ ID NO 2
<211> LENGTH: 141
<212> TYPE: PRT
<213> ORGANISM: SPERM WHALE HB ALPHA CHAIN

<400> SEQUENCE: 2

```
VAL LEU SER PRO ALA ASP LYS THR ASN VAL LYS ALA ALA TRP ALA LYS
1               5                   10                  15

VAL GLY ASN HIS ALA ALA ASP PHE GLY ALA GLU ALA LEU GLU ARG MET
            20                  25                  30

PHE MET SER PHE PRO SER THR LYS THR TYR PHE SER HIS PHE ASP LEU
        35                  40                  45

GLY HIS ASN SER THR GLN VAL LYS GLY HIS GLY LYS LYS VAL ALA ASP
    50                  55                  60

ALA LEU THR LYS ALA VAL GLY HIS LEU ASP THR LEU PRO ASP ALA LEU
65                  70                  75                  80

SER ASP LEU SER ASP LEU HIS ALA HIS LYS LEU ARG VAL ASP PRO VAL
```

```
                         85                  90                  95
ASN PHE LYS LEU LEU SER HIS CYS LEU LEU VAL THR LEU ALA ALA HIS
             100                 105                 110
LEU PRO GLY ASP PHE THR PRO SER VAL HIS ALA SER LEU ASP LYS PHE
             115                 120                 125
LEU ALA SER VAL SER THR VAL LEU THR SER LYS TYR ARG
             130                 135                 140

<210> SEQ ID NO 3
<211> LENGTH: 147
<212> TYPE: PRT
<213> ORGANISM: HUMAN HB BETA CHAIN

<400> SEQUENCE: 3

MET VAL HIS LEU THR PRO GLU GLU LYS SER ALA VAL THR ALA LEU TRP
 1                   5                  10                  15
GLY LYS VAL ASN VAL ASP GLU VAL GLY GLY GLU ALA LEU GLY ARG LEU
             20                  25                  30
LEU VAL VAL TYR PRO TRP THR GLN ARG PHE PHE GLU SER PHE GLY ASP
             35                  40                  45
LEU SER THR PRO ASP ALA VAL MET GLY ASN PRO LYS VAL LYS ALA HIS
     50                  55                  60
GLY LYS LYS VAL LEU GLY ALA PHE SER ASP GLY LEU ALA HIS LEU ASP
65                   70                  75                  80
ASN LEU LYS GLY THR PHE ALA THR LEU SER GLU LEU HIS CYS ASP LYS
                 85                  90                  95
LEU HIS VAL ASP PRO GLU ASN PHE ARG LEU LEU GLY ASN VAL LEU VAL
             100                 105                 110
CYS VAL LEU ALA HIS HIS PHE GLY LYS GLU PHE THR PRO PRO VAL GLN
             115                 120                 125
ALA ALA TYR GLN LYS VAL VAL ALA GLY VAL ALA ASN ALA LEU ALA HIS
             130                 135                 140
LYS TYR HIS
145

<210> SEQ ID NO 4
<211> LENGTH: 146
<212> TYPE: PRT
<213> ORGANISM: SPERMA WHALE HB BETA CHAIN

<400> SEQUENCE: 4

VAL HIS LEU THR GLY GLU GLU LYS SER GLY LEU THR ALA LEU TRP ALA
 1                   5                  10                  15
LYS VAL ASN VAL GLU GLU ILE GLY GLY GLU ALA LEU GLY ARG LEU LEU
             20                  25                  30
VAL VAL TYR PRO TRP THR GLN ARG PHE PHE GLU HIS PHE GLY ASP LEU
             35                  40                  45
SER THR ALA ASP ALA VAL MET LYS ASN PRO LYS VAL LYS LYS HIS GLY
     50                  55                  60
GLN LYS VAL LEU ALA SER PHE GLY GLU GLY LEU LYS HIS LEU ASP ASN
65                   70                  75                  80
LEU LYS GLY THR PHE ALA THR LEU SER GLU LEU HIS CYS ASP LYS LEU
                 85                  90                  95
HIS VAL ASP PRO GLU ASN PHE ARG LEU LEU GLY ASN VAL LEU VAL VAL
             100                 105                 110
VAL LEU ALA ARG HIS PHE GLY LYS GLU PHE THR PRO GLU LEU GLN THR
```

```
                115                 120                 125
ALA TYR GLN LYS VAL VAL ALA GLY VAL ALA ASN ALA LEU ALA HIS LYS
    130                 135                 140

TYR HIS
145

<210> SEQ ID NO 5
<211> LENGTH: 146
<212> TYPE: PRT
<213> ORGANISM: HUMAN ADULT HB BETA CHAIN

<400> SEQUENCE: 5

VAL HIS LEU THR PRO GLU GLU LYS SER ALA VAL THR ALA LEU TRP GLY
 1               5                  10                  15

LYS VAL ASN VAL ASP GLU VAL GLY GLY GLU ALA LEU GLY ARG LEU LEU
            20                  25                  30

VAL VAL TYR PRO TRP THR GLN ARG PHE PHE GLU SER PHE GLY ASP LEU
        35                  40                  45

SER THR PRO ASP ALA VAL MET GLY ASN PRO LYS VAL LYS ALA HIS GLY
    50                  55                  60

LYS LYS VAL LEU GLY ALA PHE SER ASP GLY LEU ALA HIS LEU ASP ASN
65                  70                  75                  80

LEU LYS GLY THR PHE ALA THR LEU SER GLU LEU HIS CYS ASP LYS LEU
                85                  90                  95

HIS VAL ASP PRO GLU ASN PHE ARG LEU LEU GLY ASN VAL LEU VAL CYS
            100                 105                 110

VAL LEU ALA HIS HIS PHE GLY LYS GLU PHE THR PRO PRO VAL GLN ALA
        115                 120                 125

ALA TYR GLN LYS VAL VAL ALA GLY VAL ALA ASN ALA LEU ALA HIS LYS
    130                 135                 140

TYR HIS
145

<210> SEQ ID NO 6
<211> LENGTH: 146
<212> TYPE: PRT
<213> ORGANISM: HUMAN HB (FETAL) GAMMA A

<400> SEQUENCE: 6

GLY HIS PHE THR GLU GLU ASP LYS ALA THR ILE THR SER LEU TRP GLY
 1               5                  10                  15

LYS VAL ASN VAL GLU ASP ALA GLY GLY GLU THR LEU GLY ARG LEU LEU
            20                  25                  30

VAL VAL TYR PRO TRP THR GLN ARG PHE PHE ASP SER PHE GLY ASN LEU
        35                  40                  45

SER SER ALA SER ALA ILE MET GLY ASN PRO LYS VAL LYS ALA HIS GLY
    50                  55                  60

LYS LYS VAL LEU THR SER LEU GLY ASP ALA THR LYS HIS LEU ASP ASP
65                  70                  75                  80

LEU LYS GLY THR PHE ALA GLN LEU SER GLU LEU HIS CYS ASP LYS LEU
                85                  90                  95

HIS VAL ASP PRO GLU ASN PHE LYS LEU LEU GLY ASN VAL LEU VAL THR
            100                 105                 110

VAL LEU ALA ILE HIS PHE GLY LYS GLU PHE THR PRO GLU VAL GLN ALA
        115                 120                 125
```

```
SER TRP GLN LYS MET VAL THR ALA VAL ALA SER ALA LEU SER SER ARG
    130                 135             140
TYR HIS
145
```

What is claimed is:

1. A method of producing a stabilized apohemoglobin subunit comprising modifying at least two to up to 15 amino acids of the amino acid sequence of adult human apohemoglobin subunit to match a counterpart from an apohemoglobin subunit from a deep sea diving mammal, wherein a stabilized apohemoglobin subunit exhibiting improved resistance to degradation or precipitation prior to heme insertion as compared to unmodified adult human apohemoglobin is produced.

2. A method according to claim 1, wherein said deep sea diving mammal is a sperm whale.

3. A method according to claim 1, wherein said modifying comprises forming a nucleic acid encoding an adult human apohemoglobin subunit with at least two to up to 15 variant amino acids that match their counterpart amino-acids of an apohemoglobin subunit from a deep sea diving mammal and expressing said nucleic acid in *E. coli*, another microorganism, or animal erythroid cells.

4. A recombinant adult human apohemoglobin production cell comprising:
a nucleic acid encoding an adult human apohemoglobin subunit with at least two to up to 15 variant amino acids that match their counterpart amino acids of an apohemoglobin subunit from a deep sea diving mammal that is more resistant to degradation or precipitation prior to heme insertion than an unmodified adult human apohemoglobin subunit; and
other cellular components sufficient to produce a recombinant adult human apohemoglobin.

5. A production cell according to claim 4, wherein the deep sea diving mammal is a sperm whale.

6. A production cell according to claim 4, wherein the production cell is an *E. coli* cell, a cell from another microorganism, or an animal erythroid cell.

7. A production cell according to claim 4, further comprising an expressible nucleic acid comprising the nucleic acid encoding an adult human apohemoglobin subunit.

8. A system for recombinant adult human apohemoglobin production comprising:
a plurality of production cells; and
a nucleic acid encoding a stabilized recombinant adult human apohemoglobin subunit more resistant to degradation or precipitation prior to heme insertion than unmodified adult human apohemoglobin;
wherein the nucleic acid encodes an adult human apohemoglobin subunit with at least two to up to 15 variant amino acids that match their counterpart amino acids of an apohemoglobin subunit from a deep sea diving mammal.

9. A system according to claim 8, further comprising a second nucleic acid encoding a second recombinant adult human apohemoglobin subunit.

10. A system according to claim 8, further comprising a second nucleic acid encoding a wild-type adult human apohemoglobin subunit.

11. A system according to claim 8, wherein the system produces recombinant adult human apohemoglobin that may be used as part of a blood substitute product.

\* \* \* \* \*